(12) United States Patent
Lee et al.

(10) Patent No.: US 8,753,649 B2
(45) Date of Patent: Jun. 17, 2014

(54) POLYSACCHARIDE-PROTEIN CONJUGATE VACCINES

(71) Applicant: The United States of America, as represented by the Secretary of the Department of Health and Human Services, Washington, DC (US)

(72) Inventors: Che-Hung Robert Lee, Bethesda, MD (US); Carl E. Frasch, Martinsburg, WV (US)

(73) Assignee: The United States of America, as Represented by the Secretary, Department of Health and Human Services, Washington, DC (US)

( * ) Notice: Subject to any disclaimer, the term of this patent is extended or adjusted under 35 U.S.C. 154(b) by 0 days.

(21) Appl. No.: 13/892,163

(22) Filed: May 10, 2013

(65) Prior Publication Data
US 2013/0337004 A1     Dec. 19, 2013

Related U.S. Application Data

(62) Division of application No. 13/243,480, filed on Sep. 23, 2011, now Pat. No. 8,465,749, which is a division of application No. 10/566,899, filed as application No. PCT/US2004/025477 on Aug. 6, 2004, now Pat. No. 8,048,432.

(60) Provisional application No. 60/493,389, filed on Aug. 6, 2003.

(51) Int. Cl.
*A61K 39/02*     (2006.01)
*A61K 39/112*    (2006.01)
*A61K 39/106*    (2006.01)

(52) U.S. Cl.
USPC .................. 424/234.1; 424/244.1; 424/258.1; 424/260.1

(58) Field of Classification Search
USPC ....................... 424/234.1, 244.1, 258.1, 260.1
See application file for complete search history.

(56) References Cited

U.S. PATENT DOCUMENTS

| | | | |
|---|---|---|---|
| 4,356,170 A | 10/1982 | Jennings et al. | |
| 4,771,127 A | 9/1988 | Cryz et al. | |
| 5,773,007 A | 6/1998 | Penney et al. | |
| 5,849,301 A | 12/1998 | Lees | |
| 6,207,157 B1 | 3/2001 | Gu et al. | |
| 6,531,131 B1 | 3/2003 | Gu et al. | |
| 6,607,725 B2 | 8/2003 | Gu et al. | |
| 6,685,949 B1 | 2/2004 | Gu et al. | |
| 6,756,040 B2 | 6/2004 | Peetermans et al. | |

FOREIGN PATENT DOCUMENTS

| EP | 0814833 | 5/2003 |
|---|---|---|
| WO | WO 93/13797 | 7/1993 |
| WO | WO 96/05859 | 2/1996 |
| WO | WO 96/29094 | 9/1996 |
| WO | WO 2005/037320 | 4/2005 |

OTHER PUBLICATIONS

Bartolini et al., "Immunogenicity of meningococcal B polysaccharide conjugated to tetanus toxoid or CRM107 via adipic acid dihydrazide," *Vaccine* 13:463-470, 1995.
Behr et al., "Asymmetric synthesis of potent glycosidase and very potent α-mannosidase inhibitors: 4-amino-4-deoxy-L-erythrose and 4-amino-4,5-dideoxy-L-ribose," *Tetrahedron* 59:543-553, 2003.
Byrd et al., "Preparation, Characterization, and Immunogenicity of Conjugate Vaccines Directed against *Actinobacillus pleruopneumonae* Virulence Determinants," *Infection and Immunity*, pp. 3042-3051, Aug. 1992.
Chu et al., "Further Studies on the Immunogenicity of *Haemophilus influenzae* Type b and Pneumococcal Type 6A Polysaccharide-Protein Conjugates," *Infection and Immunity* 40(I):245-256, 1983.
Cryz et al., "*Pseudomonas aeruginosa* Immunotype 5 Polysaccharide-Toxin A Conjugate Vaccine," *Infection and Immunity* pp. 161-165, Apr. 1986.
Cryz et al., "Synthesis and Characterization of a *Pseudomonas aeruginosa* Alginate-Toxin A conjugate Vaccine," *Infection and Immunity* pp. 45-50, Jan. 1991.
Cryz et al., "Synthesis and Characterization of *Escheria coli* O18 O-Polysaccharide Conjugate Vaccines," *Infection and Immunity* pp. 373-377, Feb. 1990.
Cryz et al., "Vaccine Potential of *Pseudomonas aeruginosa* O-Polysaccharide-Toxin A Conjugates," *Infection and Immunity* pp. 1547-1551, Jul. 1987.
Fattom et al., "Comparative Immunogenicity of Conjugates Composed of the *Staphylococcus aureus* Type 8 Capsular Polysaccharide Bound to Carrier Proteins by Adipic Acid Dihydrazide or N-Succinimidyl-3-(2-Pyridyldithio) propionate," *Infection and Immunity* pp. 584-589, Feb. 1992.
Gu et al., "Synthesis and Characterization of Lipooligosaccharide-Based Conjugates at Vaccine Candidates for *Moraxella (Branhamella) catarrhalis*," *Infection and Immunity* pp. 1891-1897, May 1998.
Gu et al., "Synthesis, Characterization and Immunologic Properties of Detoxified Lipooligosaccharide from Nontypeable *Haemophilus influenzae* Conjugated to Proteins," *Infection and Immunity* pp. 4047-4053, Oct. 1996.
Guo and Jennings, "Protein-polysaccharide conjugation," *Methods in Molecular Medicine, Meningococcal Vaccines: Methods and Protocols*, Eds. Pollard. A.J. and Maiden, M.C.J., Humana Press Inc., Totowa, N.J. 66:49-54, 2001.
Gupta et al., "Phase I Evaluation of *Vibrio cholera* O1, Serotype Inaba, Polysaccharide-Cholera Toxin Conjugates in Adjust Volunteers," *Infection and Immunity* pp. 3095-3099, Jul. 1998.

(Continued)

*Primary Examiner* — Rod P Swartz
(74) *Attorney, Agent, or Firm* — Klarquist Sparkman LLP

(57) ABSTRACT

Methods for synthesis and manufacture of polysaccharide-protein conjugate vaccines at high yield are provided. The methods involve reaction of a hydrazide group on one reactant with an aldehyde or cyanate ester group on the other reactant. The reaction proceeds rapidly with a high conjugation efficiency, such that a simplified purification process can be employed to separate the conjugate product from the unconjugated protein and polysaccharide and other small molecule by-products.

10 Claims, 10 Drawing Sheets

(56) References Cited

OTHER PUBLICATIONS

Jennings and Lugowski, "Immunochemistry of groups A, B, and C meningococcal polysaccharide-tetanus toxoid conjugates," *J. Immunol.* 127:1011-1018, 1981.

Konadu et al., "Phase 1 and 2 studies of *Salmonella enterica* serovar Paratyphi A O-specific polysaccharide-tetanus toxoid conjugates in adults, teenagers, and 2- to 4-year old children in Vietnam," *Infect. Immun.* 68:1529-1534, 2000.

Konadu et al., "Preparation, Characterization, and Immunological Properties in Mice of *Escherichia coli* O157 O-Specific Polysaccharide-Protein Conjugate Vaccines," *Infection and Immunity* pp. 3095-3099, Jul. 1998.

Konadu et al., "Synthesis, Characterization, and Immunological Properties in Mice of Conjugates Composed of Detoxified Lipopolysaccharide of *Salmonella paratyphi* A Bound to Tetanus Toxoid, with Emphasis on the Role of O Acetyls," *Infection and Immunity* pp. 2709-2715, Jul. 1996.

Kossaczka et al., "Evaluation of Synthetic Schemes to Prepare Immunogenic Conjugates of *Vibrio cholerae* O139 Capsular Polysaccharide with Chicken Serum Albumin," *Glycoconjugate Journal* 17(6):425-433, Jan. 2000.

Kossaczka et al., "Safety and Immunogenicity of VI Conjugate Vaccines for Typhoid Fever in Adults, Teenagers, and 2- to 4- Year Old Children in Vietnam," *Infection and Immunity* pp. 5806-5810, Nov. 1999.

Kossaczka et al., "Synthesis and Immunological Properties of Vi and Di-O-Acetyl Pectin Protein Conjugates with Adipic Acid Dihydrazide as the Linker," *Infection and Immunity* pp. 2088-2093, Jun. 1997.

Kossaczka et al., "*Vibrio cholera* O139 Conjugate Vaccines: Synthesis and Immunogenicity of *V. cholera* O139 Capsular Polysaccharide Conjugates with Recombinant Diphtheria Toxin Mutant in Mice," *Infection and Immunity* pp. 5037-5043, Sep. 2000.

Kuo et al., "Characterization of a Recombinant Pneumolysin and Its Use as Protein Carrier for Pneumococcal Type 18C Conjugate Vaccines," *Infection and Immunity* pp. 2706-2713, Jul. 1995.

Lagergard et al., "Synthesis and Immunological Properties of Conjugates Composed of Group B Streptococcus Type III Capsular Polysaccharides Covalently Bound to Tetanus Toxoid," *Infection and Immunity* pp. 687-694, Mar. 1990.

Lee, "Quality control of polyvalent pneumococcal polysaccharide-protein conjugate vaccine by nephelometry," *Biologicals* 30:97-103, 2002.

Lees et al., "Activation of soluble polysaccharides with 1-cyano-4-dimethylaminopyridinium tetrafluoroborate for use in protein-polysaccharide conjugate vaccines and immunological reagents," *Vaccine* 14:190-198, 1996.

Mulard et al., "Vaccins polyosidiques," *Ann. L'Institut Pasteur Act*, 12:37-54, 2002.

Que et al., "Effect of Carrier Selection on Immunogenicity of Protein Conjugate Vaccines against *Plasmodium falciparum* Circumsporozoites," *Infection and Immunity* pp. 2645-2649, Oct. 1988.

Sarvamangala et al., "*Cryptococcus neoformans* Serotype A Glucuronoxylamannan-Protein Conjugate Vaccines: Synthesis, Characterization, and Immunogenicity," *Infection and Immunity* pp. 3700-3707, Oct. 1991.

Schneerson et al., "Synthesis of a Conjugate Vaccine Composed of Pneumococcus Type 14 Capsular Polysaccharide Bound to Pertussis Toxin," *Infection and Immunity* pp. 3528-3532, Sep. 1992.

Shafer et al., "Activation of soluble polysaccharides with 1-cyano-4-dimethylaminopyridinium tetrafluoroborate (CDAP) for use in protein-polysaccharide conjugate vaccines and immunological reagents. II. Selective crosslinking of proteins to CDAP-activated polysaccharides," *Vaccine* 18:1273-1281, 2000.

Shafer et al., "Activiation of soluble polysaccharides with 1-cyano-4-dimethylaminopyr idinium tetrafluoroborate (CDAP) for use in protein-polysaccharide conjugate vaccines and immunological reagents. II. Selective crosslinking of proteins to CDAP-activated polysaccharides," *Vaccine* 18(13):1273-1281, Jan. 2000.

Shen et al., "Group B *Streptococcus* Capsular Polysaccharide-Cholera Toxin B Subunit Conjugate Vaccines Prepared by Different Methods for Intranasal Immunization," *Infection and Immunity* pp. 297-306, Jan. 2001.

Tutton, "The Isolation of Hydrazine," *Nature* 1105:205-210, 1891.

Communication from European Patent Office Pursuant to Article 94(3) EPC, Dated Jan. 17, 2008 in EP Application No. 04809568.1-2402.

Extended European Search Report from corresponding European Application No. 10180008.4 dated Feb. 10, 2002.

Extended European Search Report from corresponding European Application No. 10180020.9 dated Feb. 10, 2012.

Office Action dated Oct. 7, 2009, from U.S. Appl. No. 10/566,898.

Figure 1. Comparison between conjugation Method A and conventional reductive amination conjugation by HPSEC at 280 nm using a Waters Ultrahydrogel 2000 column
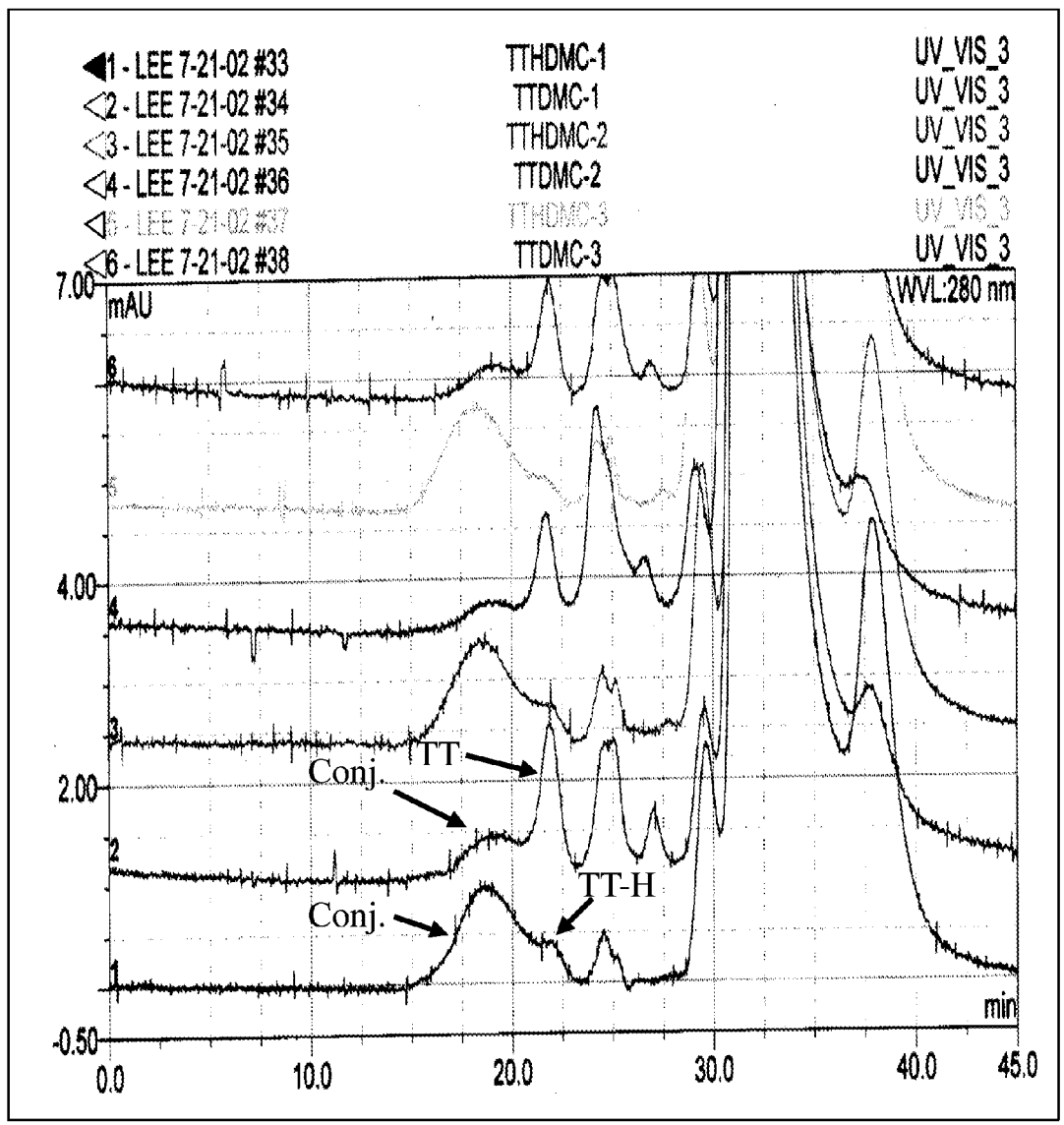

Figure 2. Effect of a blocking agent on the yield of conjugates prepared by Method B and analyzed by HPSEC at 280 nm using a Waters Ultrahydrogel 2000 column
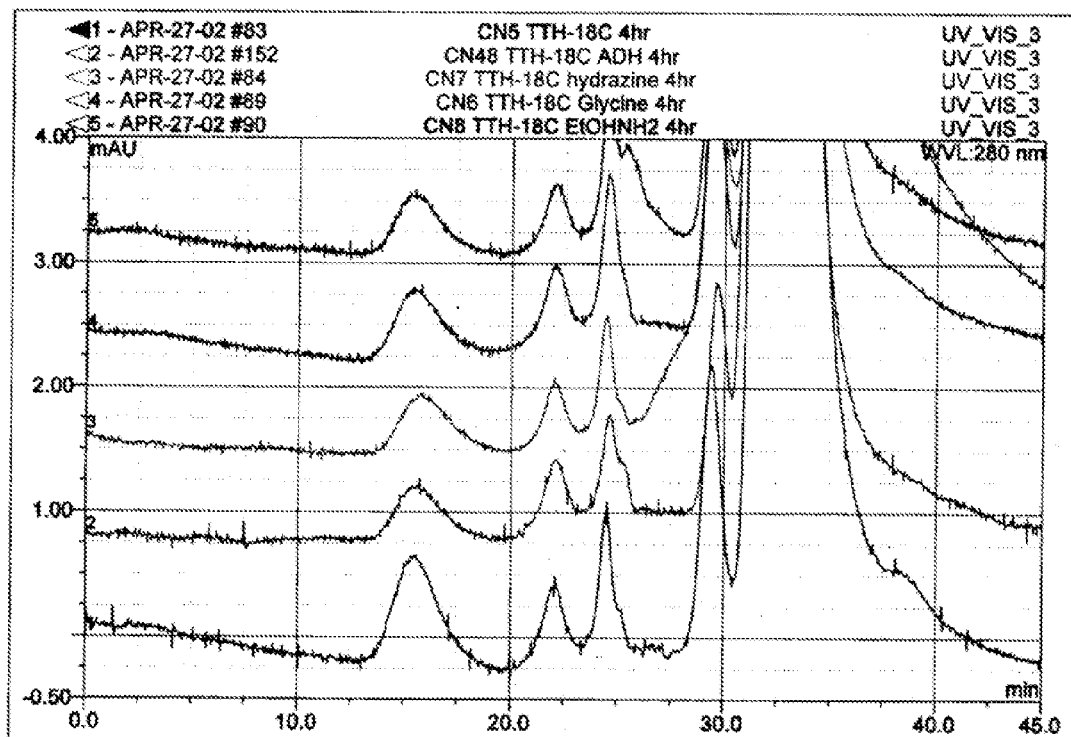

Figure 3. HPSEC profiles of four Mn C PS-TT conjugates prepared by conjugation Method A at 280 nm using a Waters Ultrahydrogel 2000 column
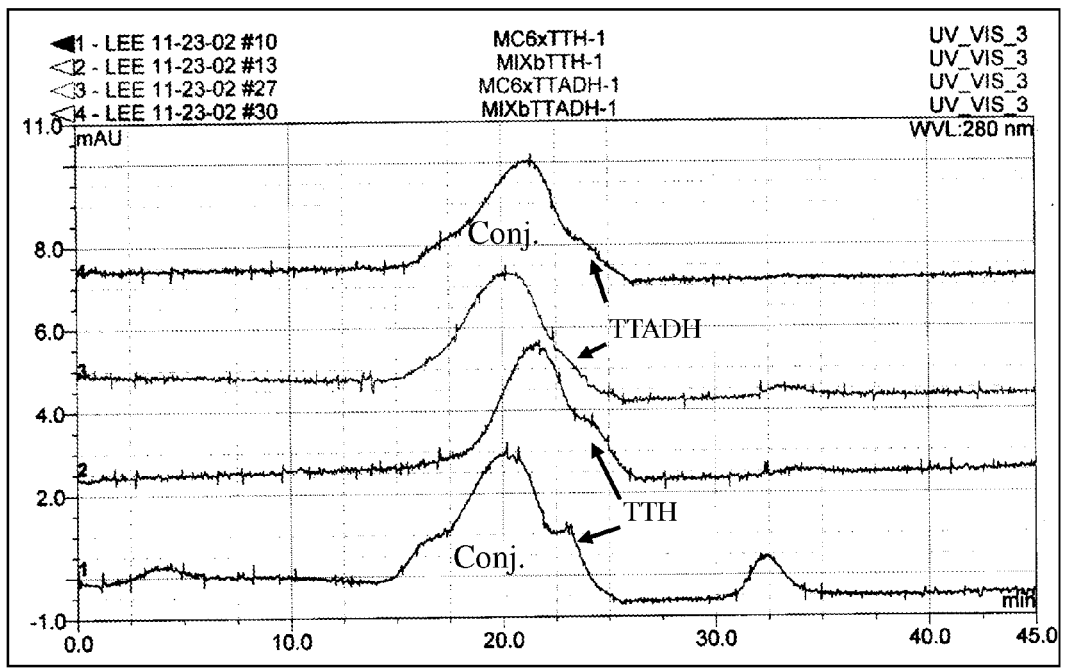

Figure 4. Estimation of free polysaccharide in a Mn C PS-TT conjugate product prepared by conjugation Method A and analyzed by HPSEC using a Waters Ultrahydrogel 2000 column
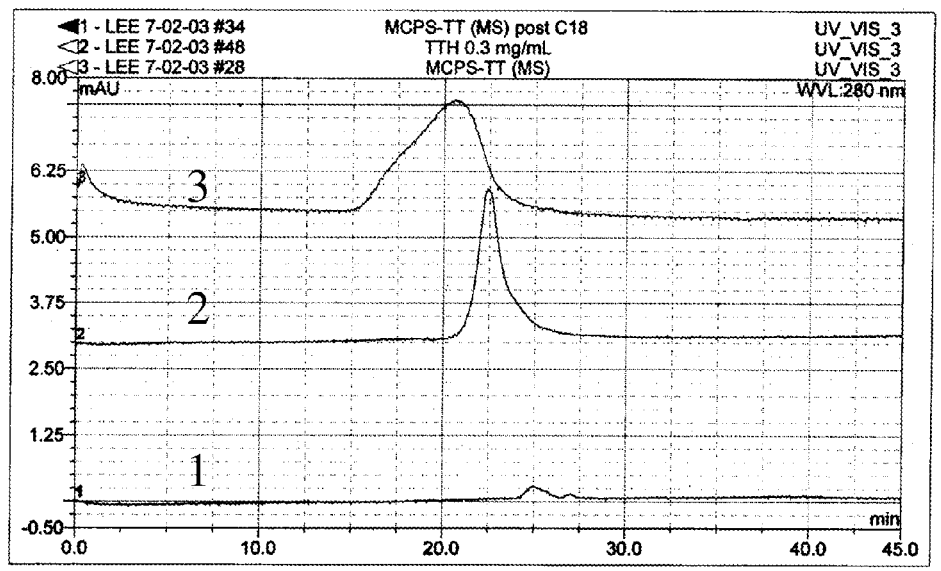
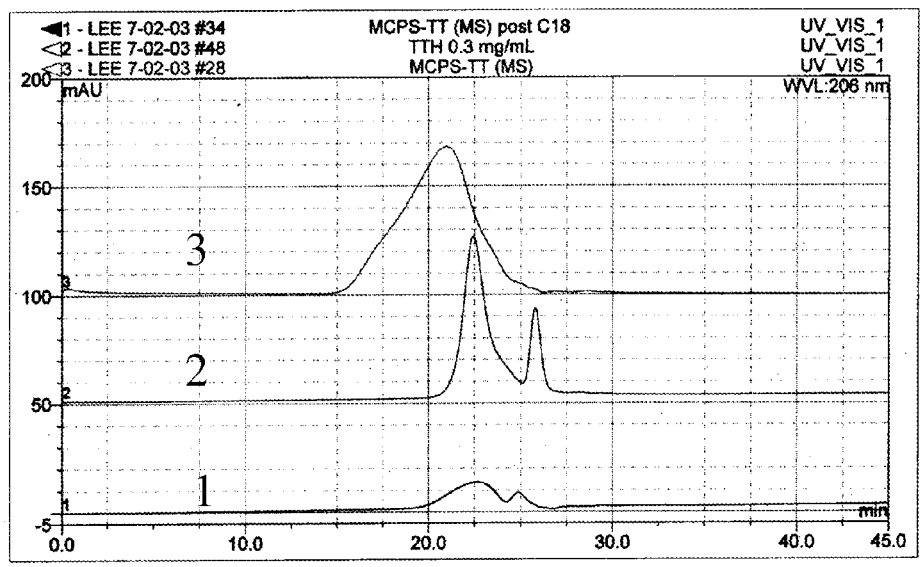

Figure 5. Quantitation of free PS in the Mn C PS-TT conjugate product prepared by Method A
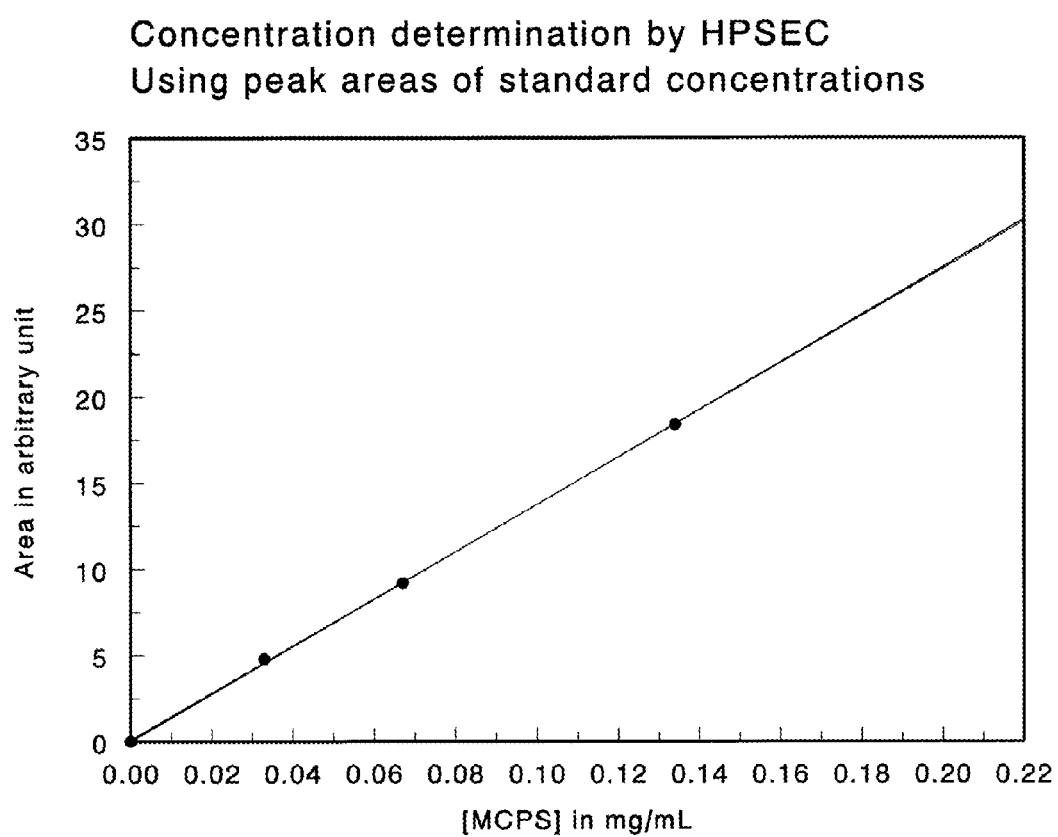

Figure 6. HPSEC profiles (280 nm) of Mn A PS-TT conjugate MA031219R prepared by Method A and TTH using a Waters Ultrahydrogel Linear column
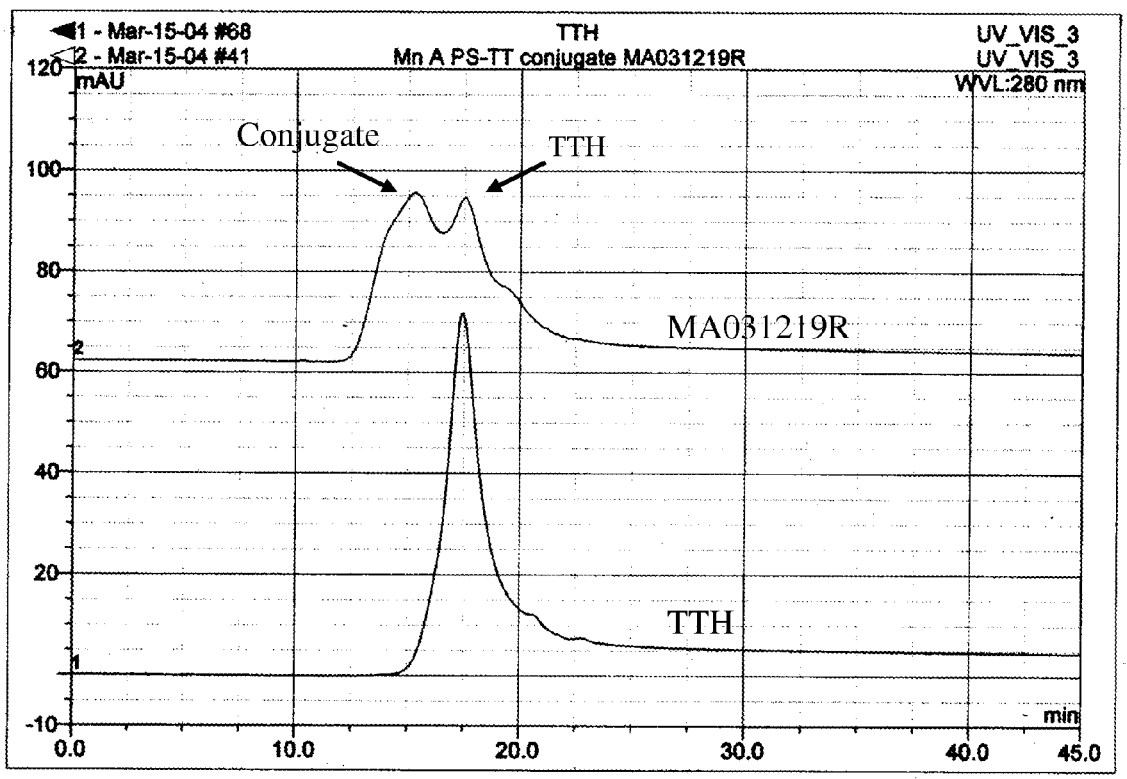

Figure 7. HPSEC profiles (280 nm) of Pn 6B PS-TT conjugate prepared by Method B and TTH using a Waters Ultrahydrogel Linear column
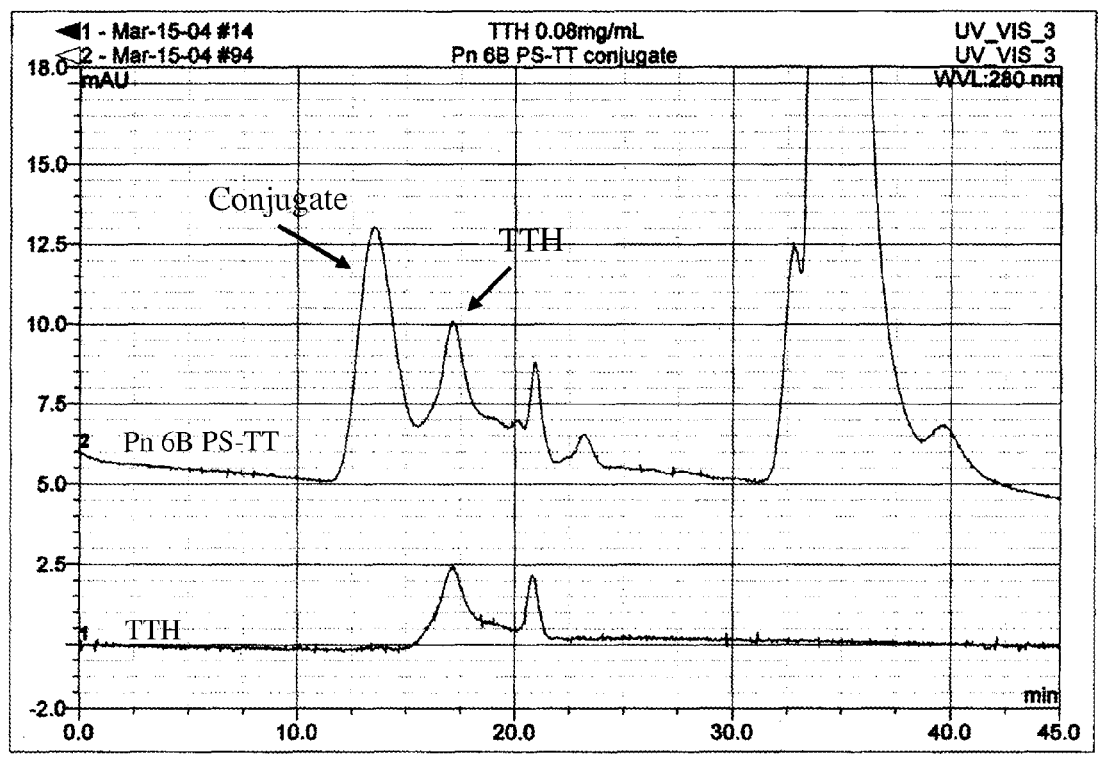

Figure 8. HPSEC profiles (280 nm) of Pn 7F PS-TT conjugate prepared by Method B and TTH using a Waters Ultrahydrogel Linear column
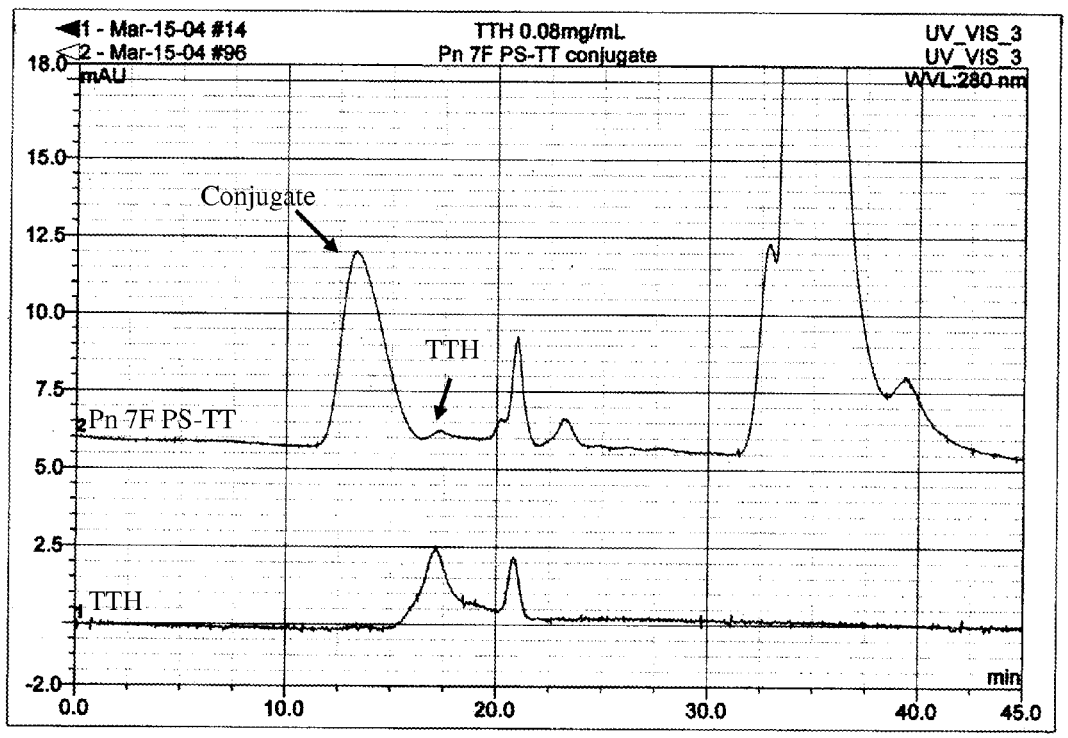

Figure 9. HPSEC profiles (280 nm) of Pn 9V PS-TT conjugate prepared by Method C and TT-aldehyde using a Waters Ultrahydrogel Linear column
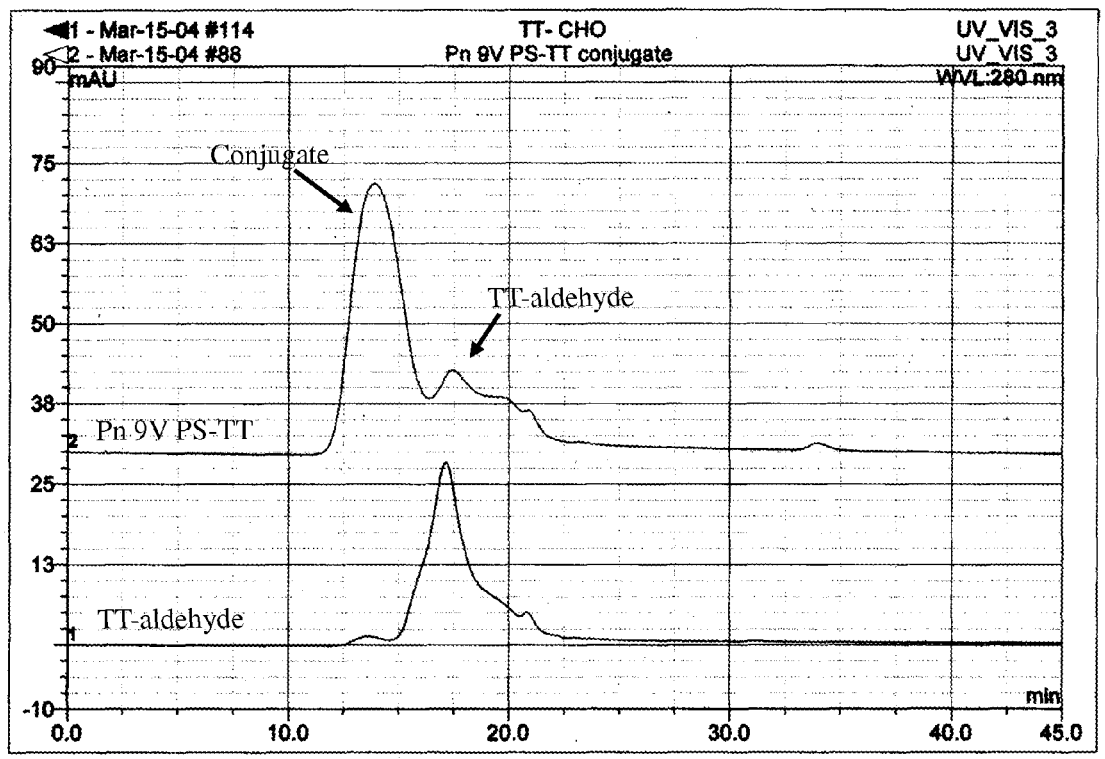

POLYSACCHARIDE-PROTEIN CONJUGATE VACCINES

CROSS-REFERENCE TO RELATED APPLICATIONS

This is a Divisional of U.S. patent application Ser. No. 13/243,480, filed Sep. 23, 2011, issued as U.S. Pat. No. 8,465,749, which is a Divisional of U.S. patent application Ser. No. 10/566,899, filed Sep. 25, 2006, issued as U.S. Pat. No. 8,048,432, which is the U.S. National Stage of International Application No. PCT/US04/25477, filed on Aug. 6, 2004, which was published in English under PCT Article 21(2), which in turn claims the benefit of U.S. Provisional Patent Application No. 60/493,389, filed Aug. 6, 2003, all of which are hereby incorporated by reference.

FIELD OF THE INVENTION

Methods for synthesis and manufacture of polysaccharide-protein conjugate vaccines at high yield are provided. The methods involve reaction of a hydrazide group on one reactant with an aldehyde or cyanate ester group on the other reactant. The reaction proceeds rapidly with a high conjugation efficiency. Simplified purification processes can be employed to separate the conjugate product from the unconjugated protein and polysaccharide and other small molecule by-products.

BACKGROUND OF THE INVENTION

Bacterial polysaccharides (PSs) are T-independent antigens inducing short-term immunity in older children and adults, but frequently not in young infants. PSs are incapable of binding to the major histocompatibility complex molecules, which is required for antigen presentation to and stimulation of T-helper lymphocytes. PSs are able to stimulate B lymphocytes for antibody production without the help of T-helper lymphocytes. As a result of the T-independent stimulation of the B lymphocytes, there is a lack of memory induction following immunization by these antigens.

T-independent polysaccharide antigens can be converted to T-dependent antigens by covalent attachment of the polysaccharides to protein molecules. B cells that bind the polysaccharide component of the conjugate vaccine can be activated by helper T cells specific for peptides that are a part of the conjugated carrier protein. The T-helper response to the carrier protein serves to augment the antibody production to the polysaccharide. PS-conjugate vaccines are polysaccharide-protein hybrids formed by the covalent attachment of a protein to a PS. Chemical modification of the PS prior to attachment is typically required because most native bacterial PSs cannot be chemically linked to a protein without first undergoing some chemical modification ("activation").

Attachment to the protein yields a number of T cell epitopes. These T cell epitopes interact with CD4 helper T cells, greatly facilitating an antibody response to the attached polysaccharide. The T helper cell-dependent response to a conjugate results in both serum IgG antibodies and immune memory, even in infants. Additionally, the immunogenicity of the PS-conjugate, in contrast to the native PS, is less dependent on the size of the conjugated PS. Accordingly, conjugates prepared with either PS or oligosaccharides can have similar immunogenicity.

There are many conjugation reactions that have been employed for covalently linking polysaccharides to proteins. Three of the more commonly employed methods include: 1) reductive amination, wherein the aldehyde or ketone group on one component of the reaction reacts with the amino or hydrazide group on the other component, and the C=N double bond formed is subsequently reduced to C—N single bond by a reducing agent; 2) cyanylation conjugation, wherein the polysaccharide is activated either by cyanogens bromide (CNBr) or by 1-cyano-4-dimethylammoniumpyridinium tetrafluoroborate (CDAP) to introduce a cyanate group to the hydroxyl group, which forms a covalent bond to the amino or hydrazide group upon addition of the protein component; and 3) a carbodiimide reaction, wherein carbodiimide activates the carboxyl group on one component of the conjugation reaction, and the activated carbonyl group reacts with the amino or hydrazide group on the other component. These reactions are also frequently employed to activate the components of the conjugate prior to the conjugation reaction.

The *Haemophilus influenzae* type b (Hib) conjugate vaccines represent the first PS-protein conjugate vaccines produced for clinical use. Robbins and his colleagues in 1980 utilized the biotechnological process of chemically attaching saccharides to protein carriers, a concept developed 50 years earlier. See Avery et al., J. Exp. Med. 1929; 50:533-550; Schneerson et al., J. Exp. Med. 1980; 152:361-376. There are now four different Hib conjugate vaccines licensed in the United States, each different, and each having their own physical, chemical, and immunological characteristics, as summarized in Table 1. A detailed review of the conjugation chemistry and quality control used in these vaccines has been published. See Kniskern et al., "Conjugation: design, chemistry, and analysis" in Ellis et al., Development and clinical uses of *Haemophilus* b conjugate vaccines. New York: Marcel Dekker, 1994: 37-69.

TABLE 1

| Vaccine | Saccharide size | Carrier protein | Spacer (linker) |
| --- | --- | --- | --- |
| PRP-D (Connaught) | Polysaccharide | Diphtheria toxoid | 6-carbon spacer (ADH) |
| HbOC (Wyeth-Lederle) | Oligosaccharide | Diphtheria protein (CRM) | None (amide) |
| PRP-OMPC (Merck) | Small polysaccharide | Meningococcal protein | Thioether (bigeneric) |
| PRP-T (Aventis Pasteur) | polysaccharide | Tetanus toxoid | 6-carbon spacer (ADH) |

\* The four Hib conjugate vaccines are described commonly in the literature with these acronyms and the responsible manufacturers are in parentheses.

The first commercial Hib conjugate, polyribosylribitol phosphate diphtheria toxoid conjugate (PRP-D), consists of partially size-reduced Hib PS attached through a six-carbon spacer, adipic acid dihydrazide (ADH), to diphtheria toxoid using the procedure of Schneerson et al., J. Exp. Med. 1980; 152:361-376. The ADH derivative of diphtheria toxoid was obtained in this method by reaction with ADH in the presence of 1-[3-(dimethylamino)propyl]-3-ethyl carbodiimide hydrochloride (EDC). The Hib PS was then activated by creating cyanate groups on the hydroxyl groups using CNBr. The activated PS was conjugated to the ADH-toxoid (cyanylation conjugation), but the process created an unstable linkage and the conjugate had solubility problems.

The Robbins conjugation chemistry was later modified such that the ADH spacer is added first to the polysaccharide, which is then conjugated to the purified protein in the presence of EDC (carbodiimide reaction). See Chu et al., Infect.

Immun. 1983; 40:245-256; Schneerson et al. Infect. Immun. 1986, 52:519-528. This modification improved the conjugation efficiency and product solubility. The vaccine polyribosylribitol phosphate tetanus protein conjugate (PRP-T) utilizes the improved chemistry to covalently link Hib polysaccharide to tetanus toxoid (see Table 1).

The polyribosylribitol phosphate cross reacting mutant diphtheria toxoid conjugate (PRP-CRM) vaccine, also referred to as *Haemophilus* b oligosaccharide conjugate (HbOC), does not contain Hib PS. Instead, it utilizes oligosaccharides of about 20 repeat units derived by periodate oxidation of the glycol functionality in the ribitol moiety. The oxidized oligosaccharides are then attached directly to $CRM_{197}$ a nontoxic mutant form of diphtheria toxin isolated from cultures of *Corynebacterium diphtheria* C7 (β197), in the presence of sodium cyanoborohydride (reductive amination). See Anderson et al., J. Immunol. 1989; 142:2464-8; and Anderson, Infect. Immun. 1983, 39:233-238. In this conjugation method, the ratio of oligosaccharide to protein was found to be critical for optimal antibody response. See Kniskern et al., "Conjugation: design, chemistry, and analysis" in Ellis et al., Development and clinical uses of *Haemophilus* b conjugate vaccines. New York: Marcel Dekker, 1994: 37-69; Anderson et al., J. Immunol. 1989; 142:2464-8.

Compared to the other Hib conjugate vaccines, Hib polysaccharide-*Neisseria meningitidis* outer membrane protein complex conjugate vaccine (PRP-OMPC) has a number of unique properties. The protein carrier is not a component of the diphtheria, tetanus, and pertussis (DTP) vaccine, but consists of lipopolysaccharide-depleted meningococcal outer membrane vesicles to which are attached size-reduced Hib PS through a thioether linkage. See Marburg et al., J. Amer. Chem. Soc. 1986; 108:52825287; Kniskern et al., "Conjugation: design, chemistry, and analysis" in Ellis et al., Development and clinical uses of *Haemophilus* b conjugate vaccines. New York: Marcel Dekker, 1994: 37-69; Anderson et al., J. Immunol. 1989; 142:2464-8. In this process, separate linkers are attached to both the protein and Hib polysaccharide, followed by fusion of the linkers to form a thioether linkage.

*Neisseria meningitidis* is a leading cause of bacterial meningitis and sepsis throughout the world. Pathogenic meningococci are enveloped by a polysaccharide capsule that is attached to the outer membrane surface of the organism. Thirteen different serogroups of meningococci have been identified on the basis of the immunological specificity of the capsular polysaccharide (Frasch, C. E., et. al., "Serotype antigens of *Neisseria meningitides* and a proposed scheme for designation of serotypes," *Rev Infect Dis.* 7(4):504-10, July-August 1985). Of these thirteen serogroups, five cause the majority of meningococcal disease; these include serogroups A, B, C, W135, and Y. Serogroup A is responsible for most epidemic disease. Serogroups B, C, and Y cause the majority of endemic disease and localized outbreaks. Host defense of invasive meningococci is dependent upon complement-mediated bacteriolysis. The serum antibodies that are responsible for complement-mediated bacteriolysis are directed in large part against the outer capsular polysaccharide.

Conventional vaccines based on meningococcal polysaccharide elicit an immune response against the capsular polysaccharide. These antibodies are capable of complement-mediated bacteriolysis of the serogroup specific meningococci. The meningococcal polysaccharide vaccines were shown to be efficacious in children and adults. However, efficacy was limited in infants and young children, and subsequent doses of the polysaccharide in younger populations elicited a weak or no booster response.

There are a number of approaches that have been employed for activation of the meningococcal PS and for conjugation, as summarized in Table 2. Each mode of activation has the potential to alter important epitopes, even when relatively few sites are activated on the PS molecule. Periodate activation of the group C meningococcal PS, for example, results in chain breakage generating smaller saccharide units with terminal aldehyde groups that can be linked to the protein via reductive amination. Richmond et al., J. Infect. Dis. 1999; 179:1569-72.

TABLE 2

| Method | Saccharide size | Carrier protein | Spacer | Procedure | Used in humans |
|---|---|---|---|---|---|
| #1 Reductive amination | Reduced | Tetanus toxoid | None | Aldehyde form of PS combined with protein in presence of sodium cyanoborohydride | No |
| #2 Carbodiimide | Native | Tetanus toxoid | None | PS and protein combined in presence of carbodiimide, then blocked with ethanolamine | No |
| #3 Active ester [a] | Oligosaccharide | $CRM_{197}$ | Adipic acid | Aminated reducing terminus of the oligosaccharide conjugated to protein by adipic acid $(NHS)_2$ | Yes |
| #4 Reductive amination | Reduced | $CRM_{197}$ | None | Aldehyde form of saccharide combined with protein in presence of sodium cyanoborohydride | Yes |
| #5 Reductive amination | De-OAc PS [b] | Tetanus toxoid | None | Aldehyde form of PS combined with protein in presence of sodium cyanoborohydride | Yes |

[a] N-hydroxysuccinimide diester of adipic acid
[b] Deacetylylated PS only reported for Meningococcal group C Initial studies on production and optimization of meningococcal group C conjugates were reported well before commercialization of the Hib conjugates. See Beuvery et al., Infect. Immun. 1982; 37:15-22; Beuvery et al., Infect. Immun. 1983; 40:39-45; Beuvery et al., J. Infect. 1983; 6:247-55; Jennings, et al., J. Immunol. 1981; 127:1011-8.

Two different conjugation methodologies have been reported for chemically linking the group C PS to a protein carrier. See Jennings et al., J. Immunol. 1981; 127:1011-8; Beuvery et al., Infect. Immun. 1983; 40:39-45. The first approach employs partially depolymerized PS, which is activated by creation of terminal aldehyde groups through periodate oxidation (Method #1 in Table 2). The aldehydes are then reacted through reductive amination combined with free amino groups on the protein, mostly lysines, in the presence of sodium cyanoborohydride. See Jennings et al., J Immunol 1981; 127:1011-8. In this method, activation occurs at one specific site on the group C PS.

The second approach utilizes the carbodiimide reaction (Method #2 in Table 2) to covalently link carboxylic groups in the high molecular weight PS to lysine e-amino groups on the carrier protein. The activation sites in this method are more random, compared to periodate activation.

Group C meningococcal conjugates prepared by these two methods have been evaluated in animals. See Beuvery et al., Dev. Biol. Stand. 1986; 65:197-204; and Beuvery et al., J. Infect. 1983; 6:247-55. The conjugates stimulated both T cell independent and T cell dependent responses upon initial immunization. See Beuvery et al., J. Infect. 1983; 6:247-55.

Studies have shown that the PS must, however, be covalently linked to the carrier protein to induce a T cell dependent antibody response.

The first group A and group C meningococcal conjugates to be used in clinical trials were prepared by Chiron Vaccines and were reported in 1992 (Method #3 in Table 2). See Costantino et al., Vaccine 1992; 10:691-8. The conjugation method was based upon selective terminal group activation of small oligosaccharides produced by mild acid hydrolysis followed by coupling to a protein through a hydrocarbon spacer. The non-toxic mutant of diphtheria toxin, $CRM_{197}$, was used as the protein carrier. To activate the oligosaccharides for conjugation, an amino group was added to the end of the oligosaccharide, and then reacted with the N-hydroxysuccinimide diester of adipic acid to create an active ester. This active ester was then covalently bound to lysine e-amino groups in the $CRM_{197}$ protein, creating the conjugate.

SUMMARY OF THE INVENTION

Conventional methods for the preparation of PS-protein conjugate vaccines do not use hydrazide chemistry in the reductive amination conjugation reaction, even though hydrazide in the form of ADH has been used in activating polysaccharide. These prior art methods utilize s-amino groups of lysine residues on the protein to react with functional groups on activated PSs, such as aldehyde groups (reductive amination) and carboxyl groups. The efficiency of the reaction is low, typically only about 20%. The reaction also requires two to three days for the conjugation to be completed, necessitating the use of purification steps to separate the conjugate from unreacted PS. See Guo et al., "Protein-polysaccharide conjugation" in: Pollard et al., Methods in Molecular Medicine, Vol. 66: Meningococcal Vaccines: methods and Protocols, Humana Press, Totowa, N.J., 2001, pg 49-54. There are a number of explanations that have been proposed for the low yields observed. First, the e-amino group of lysine (pKa=10.5) has low reactivity at the conjugation conditions (pH 6.5-7.4). See Inman et al., Biochemistry 1969; 8:4074-4082. Secondly, most conjugation methods employ toxoids as the carrier proteins. The toxoids are derived from a toxin by detoxification with formaldehyde, which combines with the amino groups of the toxin, leaving a limited numbers of amino groups available for conjugation. Thirdly, reduced solubility of the resulting activated protein and protein-PS conjugate can lead to precipitation.

Accordingly, methods for the synthesis and manufacture of polysaccharide-protein conjugate vaccines in high yields are desirable. Also desirable are methods wherein the reaction proceeds at a rapid rate, with reduced production of undesired by-products, and with reduced amounts of unreacted protein and polysaccharide remaining at the end of the reaction.

Existing vaccines based on PSs are of limited use in young children and do not provide long-lasting protection in adults. Thus, a need exists for a protein-PS conjugate vaccine capable of conferring long term protection against diseases in children and adults at risk for, e.g., bacterial meningitis, influenza, tetanus, and other bacterial infections. The protein-PS conjugates of the preferred embodiment can be employed to prepare vaccine formulations capable of conferring long term protection to infants, children, and adults.

Accordingly, in a first embodiment, a method for preparing a conjugate vaccine is provided, the method comprising reacting a polysaccharide with an oxidizing agent, whereby a solution of an aldehyde-activated polysaccharide is obtained; buffer exchanging the solution of the aldehyde-activated polysaccharide to a pH of from about 7 to about 8; reacting a protein with hydrazine or adipic acid dihydrazide in the presence of 1-[3-(dimethylamino)propyl]-3-ethyl carbodiimide hydrochloride at a pH of from about 6 to about 7, whereby a solution of an hydrazide-activated protein is obtained; raising a pH of the solution of the hydrazide-activated protein to from about 7.0 to about 11; buffer exchanging the solution of the hydrazide-activated protein to a pH of from about 10.0 to about 11.0; reacting the aldehyde-activated polysaccharide with the hydrazide-activated protein at a pH of from about 6 to about 8, whereby a conjugate comprising one or more C=N double bonds is obtained; and reducing substantially all of the C=N double bonds of the conjugate to C—N single bonds, whereby a conjugate vaccine capable of stimulating an immune response is obtained.

In an aspect of the first embodiment, the oxidizing agent comprises $NaIO_4$.

In an aspect of the first embodiment, the solution of the aldehyde-activated polysaccharide is buffer exchanged with a HEPES buffer.

In an aspect of the first embodiment, the solution of the hydrazide-activated protein is buffer exchanged with a $Na_2CO_3$ buffer.

In an aspect of the first embodiment, the aldehyde-activated polysaccharide is reacted with the hydrazide-activated protein at a ratio of from about 1:2 to about 2:1.

In an aspect of the first embodiment, reducing comprises reducing with $NaBH_4$.

In an aspect of the first embodiment, the polysaccharide is selected from the group consisting of Meningococcal polysaccharides, Pneumococcus polysaccharides, *Hemophilus influenzae* type b polysaccharide, Vi polysaccharide of *Salmonnella typhi*, and group B *Streptococcus* polysaccharides.

In an aspect of the first embodiment, the protein is selected from the group consisting of tetanus toxoid, diptheria toxoid, $CRM_{197}$, and meningococcal protein.

In a second embodiment, a method for preparing a conjugate vaccine is provided, the method comprising reacting a polysaccharide with 1-cyano-4-dimethylammoniumpyridinium tetrafluoroborate, whereby a solution of a cyanate-activated polysaccharide is obtained; reacting a protein with hydrazine or adipic acid dihydrazide in the presence of 1-[3-(dimethylamino)propyl]-3-ethyl carbodiimide hydrochloride at a pH of from about 6 to about 7, whereby a solution of a hydrazide-activated protein is obtained; raising the pH of the solution of the hydrazide-activated protein to from about 7.0 to about 11; buffer exchanging the solution of the hydrazide-activated protein to a pH of from about 10.0 to about 11.0; reacting the cyanate-activated polysaccharide with the hydrazide-activated protein at a pH of from about 6 to about 8 to yield a conjugate vaccine capable of stimulating an immune response.

In an aspect of the second embodiment, the step of reacting the cyanate-activated polysaccharide with the hydrazide-activated protein is conducted in the absence of a blocking agent.

In an aspect of the second embodiment, the polysaccharide is selected from the group consisting of Meningococcal polysaccharides, Pneumococcus polysaccharides, *Hemophilus influenzae* type b polysaccharide, Vi polysaccharide of *Salmonella typhi*, and group B *Streptococcus* polysaccharides.

In an aspect of the second embodiment, the protein is selected from the group consisting of tetanus toxoid, diptheria toxoid, $CRM_{197}$, and meningococcal protein.

In a third embodiment, a method for preparing a conjugate vaccine is provided, the method comprising reacting a protein with 1-amino-2,3-propanediol (APDO) in the presence of 1-[3-(dimethylamino)propyl]-3-ethyl carbodiimide hydrochloride at a pH of from about 6 to about 7, whereby a solution of a APDO-modified protein is obtained; buffer exchanging the solution of the APDO-modified protein to a pH of from about 10.0 to about 11.0; reacting the APDO-modified protein with an oxidizing agent, whereby a solution of an aldehyde-activated protein is obtained; buffer exchanging the solution of the aldehyde-activated protein to a pH of from about 10.0 to about 11.0; reacting a hydrazide-activated polysaccharide with the aldehyde-activated protein at a pH of from about 6 to about 8, whereby a conjugate comprising one or more C=N double bonds is obtained; and reducing substantially all of the C=N double bonds of the conjugate to C—N single bonds, whereby a conjugate vaccine capable of stimulating an immune response is obtained.

In an aspect of the third embodiment, the polysaccharide is selected from the group consisting of Meningococcal polysaccharides, Pneumococcus polysaccharides, *Hemophilus influenzae* type b polysaccharide, Vi polysaccharide of *Salmonnella typhi*, and group B *Streptococcus* polysaccharides.

In an aspect of the third embodiment, the protein is selected from the group consisting of tetanus toxoid, diptheria toxoid, $CRM_{197}$, and meningococcal protein.

In an aspect of the third embodiment, the hydrazide-activated polysaccharide is prepared by reacting a polysaccharide with an oxidizing agent in a solution, whereby an aldehyde-activated polysaccharide is obtained; reacting the aldehyde-activated polysaccharide with adipic acid dihydrazide to yield an intermediate comprising one or more C=N double bonds; and reducing substantially all of the C=N double bonds of the intermediate to C—N single bonds, whereby a hydrazide-activated polysaccharide is obtained.

In an aspect of the third embodiment, the hydrazide-activated polysaccharide is prepared by reacting a polysaccharide with 1-cyano-4-dimethylammoniumpyridinium tetrafluoroborate, whereby a cyanate-functionalized polysaccharide is obtained; reacting the cyanate-functionalized polysaccharide with adipic acid dihydrazide, whereby a hydrazide-activated polysaccharide is obtained.

In an aspect of the third embodiment, the hydrazide-activated polysaccharide is prepared by reacting a polysaccharide with adipic acid dihydrazide in the presence of 1-[3-(dimethylamino)propyl]-3-ethyl carbodiimide hydrochloride, whereby a hydrazide-activated polysaccharide is obtained.

In a fourth embodiment, a conjugate vaccine is provided, the conjugate vaccine comprising at least one polysaccharide moiety and at least one protein moiety, wherein the polysaccharide moiety is linked to the protein moiety through at least one linking group of the formula —C(=O)—NH—NH—$CH_2$—.

In an aspect of the fourth embodiment, the conjugate vaccine comprises a plurality of polysaccharide moieties and a plurality of protein moieties crosslinked to form a lattice structure by a plurality of linking groups.

In an aspect of the fourth embodiment, the polysaccharide is selected from the group consisting of Meningococcal polysaccharides, Pneumococcus polysaccharides, *Hemophilus influenzae* type b polysaccharide, Vi polysaccharide of *Salmonnella typhi*, and group B *Streptococcus* polysaccharides.

In an aspect of the fourth embodiment, the protein is selected from the group consisting of tetanus toxoid, diptheria toxoid, $CRM_{197}$, and meningococcal protein.

In a fifth embodiment, a conjugate vaccine is provided, the conjugate vaccine comprising at least one polysaccharide moiety and at least one protein moiety, wherein the polysaccharide moiety is linked to the protein moiety through at least one linking group of the formula —C(=O)—NH—NH—C(=NH)—O—.

In an aspect of the fifth embodiment, the conjugate vaccine comprises a plurality of polysaccharide moieties and a plurality of protein moieties crosslinked to Rum a lattice structure by a plurality of linking groups.

In an aspect of the fifth embodiment, the polysaccharide is selected from the group consisting of Meningococcal polysaccharides, Pneumococcus polysaccharides, *Hemophilus influenzae* type b polysaccharide, Vi polysaccharide of *Salmonnella typhi*, and group B *Streptococcus* polysaccharides.

In an aspect of the fifth embodiment, the protein is selected from the group consisting of tetanus toxoid, diptheria toxoid, $CRM_{197}$, and meningococcal protein.

In a sixth embodiment, a conjugate vaccine is provided, the conjugate vaccine comprising at least one polysaccharide moiety and at least one protein moiety, wherein the polysaccharide moiety is linked to the protein moiety through at least one linking group of the formula —C(=O)—NH—$CH_2$—$CH_2$—NH—NH—.

In an aspect of the sixth embodiment, the conjugate vaccine comprises a plurality of polysaccharide moieties and a plurality of protein moieties crosslinked to form a lattice structure by a plurality of linking groups.

In an aspect of the sixth embodiment, the polysaccharide is selected from the group consisting of Meningococcal polysaccharides, Pneumococcus polysaccharides, *Hemophilus influenzae* type b polysaccharide, Vi polysaccharide of *Salmonnella typhi*, and group B *Streptococcus* polysaccharides.

In an aspect of the sixth embodiment, the protein is selected from the group consisting of tetanus toxoid, diptheria toxoid, $CRM_{197}$, and meningococcal protein.

BRIEF DESCRIPTION OF THE DRAWINGS

FIG. 1 provides spectra of products of the conjugation of periodate activated group C meningococcal polysaccharide to a) e-amino groups on lysines (TT) (conventional method), and b) hydrazide groups on aspartic and glutamic acid residues (TT-H). The spectra are taken from conjugation products before a dialysis step and contain extra peaks at greater than 25 minutes not seen after dialysis. The yield of the conjugate (Conj.) is much greater for TTH than TT.

FIG. 2 provides high-performance size exclusion chromatography (HPSEC) profiles of Pn 18C PS-TT conjugates prepared by cyanylation conjugation in the absence and presence of a blocking agent ADH, hydrazine, glycine or ethanolamine. The conjugate peak (Conj., 15.5 minutes) is reduced significantly in the presence of a blocking agent while the free protein peak (22 minutes) is not. The spectra are taken from conjugation products before the dialysis step and contain extra peaks at greater than 25 minutes not seen after dialysis.

FIG. 3 provides HPSEC profiles of four Mn C PS-TT conjugates prepared by reductive amination conjugation of aldehyde-activated PS and hydrazide-activated protein. The HPSEC profiles shift slightly at different time. The right shoulder at 22.5-24 minutes is from the unconjugated protein TTH or TTADH, while the left shoulder at 16-17 minutes is from high molecular weight conjugate.

FIG. 4A provides HPSEC profiles of an Mn C PS-TT conjugate pre (3) and post (1) C18 absorption, and pure TTH (2) monitored at 280 nm, detecting protein. Complete absorption of protein species by C18 from the conjugate product is shown in profile (1). FIG. 4B provides HPSEC profiles of the same three injections as in FIG. 4A monitored at 206 nm, detecting protein and polysaccharide. The peak at 22.5 minutes in post Cl8 absorption (1) is from the un-absorbed free polysaccharide in the conjugate product. FIG. 4C provides a comparison of HPSEC profile at 206 nm of free PS in conjugate product (1) with those of activated Mn C PS at 0.033 mg/ml (2), 0.067 mg/ml (3), and 0.134 mg/ml (4).

FIG. 5 provides a quantitation of free PS in the Mn C PS-TT conjugate prepared by reductive amination conjugation of aldehyde-activated PS and hydrazide-activated protein. The area of the peak at 22.5 minutes in HPSEC profiles 2, 3 and 4 in FIG. 4C is measured and plotted against its respective concentration to construct a standard curve. The content of free PS in conjugate product is calculated from the peak area at 22.5 minutes of profile 1 in FIG. 4C.

FIG. 6 provides HPSEC profiles (280 nm) of Mn A PS-TT conjugate MA031219R prepared by reductive amination conjugation of aldehyde-activated PS and hydrazide-activated protein, and TTH using a Waters Ultrahydrogel Linear column. Upon conjugation, the protein signal shifts from 17.5 minutes to 15 minutes.

FIG. 7 provides HPSEC profiles (280 nm) of Pn 6B PS-TT conjugate prepared by cyanylation conjugation and TTH using a Waters Ultrahydrogel Linear column. Upon conjugation, the protein signal shifts from 17 minutes to 13.5 minutes. The spectra are taken from conjugation products before a dialysis step and contain extra peaks at greater than 25 minutes not seen after dialysis.

FIG. 8 provides HPSEC profiles (280 nm) of Pn 7F PS-TT conjugate prepared by cyanylation conjugation. Upon conjugation, the protein signal shifts from 17 minutes to 13.5 minutes. The spectra are taken from conjugation products before the dialysis step and contain extra peaks at greater than 25 minutes not seen after dialysis.

FIG. 9 provides HPSEC profiles (280 nm) of Pn 9V PS-TT conjugate prepared by reductive amination conjugation of hydrazide-activated PS and aldehyde-activated protein TT-aldehyde. Upon conjugation, the protein signal shifts from 17 minutes to 13.5 minutes.

DETAILED DESCRIPTION OF THE PREFERRED EMBODIMENT

Figure 4:
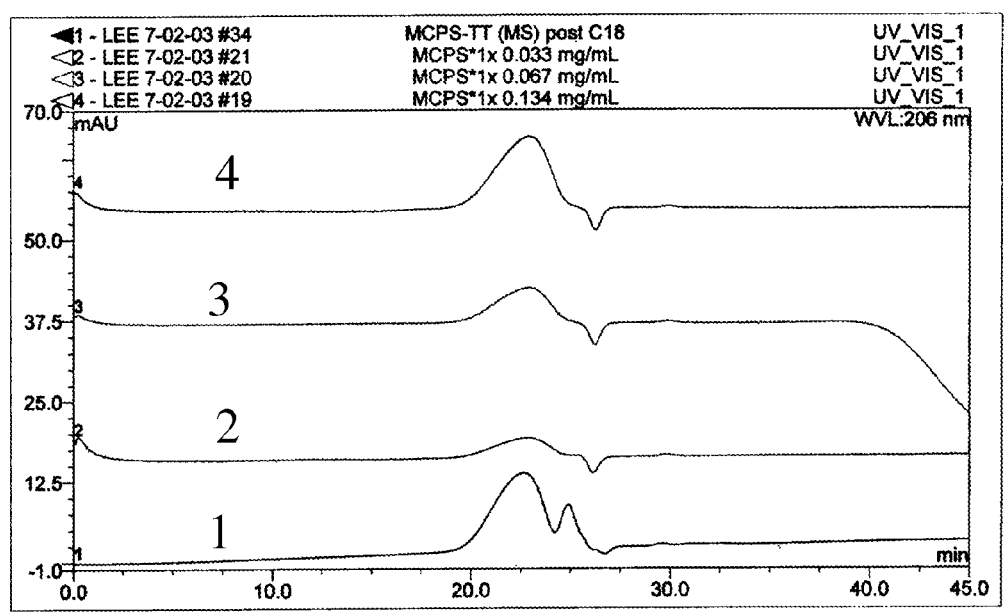
FIG. 4 provides estimation of free polysaccharide in a Mn C PS-TT conjugate product prepared by reductive amination conjugation of aldehyde-activated PS and hydrazide-activated protein.

The following description and examples illustrate a preferred embodiment of the present invention in detail. Those of skill in the art recognize that there are numerous variations and modifications of this invention that are encompassed by its scope. Accordingly, the description of a preferred embodiment should not be deemed to limit the scope of the present invention.

Introduction

Conventional methods for synthesis and manufacturing of polysaccharide-protein conjugate vaccines typically employ conjugation reactions with low efficiency (typically about 20%). This means that up to 80% of the added activated polysaccharide is lost. In addition, a chromatographic process for purification of the conjugates from unconjugated PS is typically required. The synthetic methods of the preferred embodiments utilize the characteristic chemical property of hydrazide groups on one reactant to react with aldehyde groups or cyanate esters on the other reactant with an improved conjugate yield (typically as high as about 60%).

When the conjugation reaction proceeds with a greater conjugation efficiency, the amount of unconjugated protein and polysaccharide remaining after reaction can be sufficiently low so as to make its removal unnecessary. Accordingly, the process of purifying the conjugate product can be simplified to, e.g., a diafiltration step for removal of small molecule by-products. The hydrazide-based conjugation reaction can be carried to completion within one or two days at reactant concentrations of from about 1 to about 40 mg/mL at PS/protein mole ratios of from about 1:5 to about 5:1, preferably from about 1:2 to about 2:1, and most preferably about 1:1, although in certain embodiments higher or lower ratios can be preferred. The conjugation reaction is preferably conducted at temperatures of from about 4° C. to about 40° C., preferably from about 5, 10, 15, or 20° C. to about 25, 30, or 35° C., and at a pH of from about 6 to about 8.5, preferably from about 6.1, 6.2, 6.3, 6.4, or 6.5 to about 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, or 8.4, with optimal conditions varying according to the polysaccharide. Accordingly, conjugate vaccine can be manufactured at lower cost when a hydrazide-based conjugation reaction is employed.

To overcome certain drawbacks of conventional methods for synthesizing conjugate vaccines, a method for conjugation of PSs to carrier proteins using hydrazide chemistry in reduction amination and cyanylation conjugation reactions is provided. Hydrazide groups having the structure —NH—NH2 are introduced onto the carboxyl groups of the aspartic acid and/or glutamic acid residues of protein molecules by carbodiimide reaction with hydrazine, ADH, carbohydrazide, or succinyl dihydride. The activated protein is maintained soluble at a pH of from about 10 to about 11.5, preferably from about 10.1, 10.2, 10.3, or 10.4 to about 10.6, 10.7, 10.8, 10.9, 11.0, 11.1, 11.2, 11.3, or 11.4, and most preferably about 10.5, with a buffer at a concentration of from about 3 or less to about 10 mM or more, preferably from about 4 or 5 mM to about 6, 7, 8, or 9 mM, before conjugation. Suitable buffers include but are not limited to $Na_2CO_3$, 3-(cyclohexylamino)-1-propanesulfonic acid (CAPS), and (2-(N-cyclohexylamino)ethane sulfonic acid (CHES). The activated protein is then reacted with activated polysaccharide containing either aldehyde (reductive amination) or cyanate (cyanylation conjugation) groups at a pH of from about 6 to about 8.5, preferably from about 6.1, 6.2, 6.3, 6.4, or 6.5 to about 6.6, 6.7, 6.8, 6.9, 7.0, 7.1, 7.2, 7.3, 7.4, 7.5, 7.6, 7.7, 7.8, 7.9, 8.0 in the presence of a buffer at a concentration about 100 mM or less to about 200 mM, preferably from about 110, 120, 130, 140 or 150 mM to about 160, 170, 180 or 190 mM. Suitable buffers include but are not limited to N-(2-hydroxyethyl)piperazine-N'-(2-ethanesulfonic acid) (HEPES), phosphate buffered saline (PBS), TES (EDTA, Tris-HCl, SDS), morpholinopropanesulfonic acid (MOPS), and N,N-bis(2-hydroxyethyl)-2-aminoethanesulfonic acid (BES).

Alternatively, the PS can be functionalized with hydrazide groups. The activated PS can be conjugated, at pH 6.5-7.5 with a strong buffer, to activated proteins containing aldehyde groups (reductive amination). The protein is maintained soluble at a pH of about 10.5 with a weak buffer until the point of conjugation. Because of the higher reactivity of hydrazide groups (pKa=2.6) compared to the lysine e-amino group (pKa=10.5) at neutral/mild acidic conditions, and the enhanced solubility of the conjugate using activated protein maintained soluble at about pH 10.5 before conjugation, the yield of the conjugation reaction is greatly increased. The greater reactivity of the hydrazide-activated tetanus toxoid (TT-H) compared to tetanus toxoid (TT) is illustrated in FIG. 1.

Conjugates prepared by these methods are immunogenic in experimental animals, as demonstrated in experiments on mice. In addition, the conjugation reaction can be efficiently carried out without sodium cyanoborohydride, thereby avoiding introduction of cyanide ion in the conjugate product. The reaction can be conducted under mild acidic or neutral pH conditions at room temperature or at 4° C. overnight as opposed to days for conventional reductive amination conjugation methods. This again ensures high yield conjugate vaccine production for unstable polysaccharides, such as those from *Haemophilus influenzae* type b, *Streptococcus pneumoniae* type 19F and *Neisseria meningitides* group A. The methods of preferred embodiments can be employed to produce less expensive conjugate vaccines, thereby greatly promoting public health.

The Polysaccharide

The term "polysaccharide" as used herein, is a broad term and is used in its ordinary sense, including, without limitation, saccharides comprising a plurality of repeating units, including, but not limited to polysaccharides having 50 or more repeat units, and oligosaccharides having 50 or less repeating units. Typically, polysaccharides have from about 50, 55, 60, 65, 70, 75, 80, 85, 90, or 95 repeating units to about 2,000 or more repeating units, and preferably from about 100, 150, 200, 250, 300, 350, 400, 500, 600, 700, 800, 900 or 1000 repeating units to about, 1100, 1200, 1300, 1400, 1500, 1600, 1700, 1800, or 1900 repeating unit. Oligosaccharides typically about from about 6, 7, 8, 9, or 10 repeating units to about 15, 20, 25, 30, or 35 to about 40 or 45 repeating units.

Suitable polysaccharides for use in the preferred embodiments include polysaccharides and oligosaccharides from encapsulated bacteria. The polysaccharides and oligosaccharides can be from any source, for example, they can be derived from naturally-occurring bacteria, genetically engineered bacteria, or can be produced synthetically. The polysaccharides and oligosaccharides can be subjected to one or more processing steps prior to activation, for example, purification, functionalization, depolymerization using mild oxidative conditions, deacetylation, and the like. Post processing steps can also be employed, if desired. Any suitable method known in the art for synthesizing, preparing, and/or purifying suitable polysaccharides and oligosaccharides can be employed.

Polysaccharides and oligosaccharides for use in preferred embodiments include pneumococcal polysaccharides of, for example, serotypes 1, 2, 3, 4, 5, 6B, 7F, 8, 9N, 9V, 10A, 11A, 12F, 14, 15B, 17F, 18C, 19A, 19F, 20, 22F, 23F and 33F; meningococcal polysaccharides of serotypes A, B, C, W135, and Y, *Haemophilus influenzae* type b polysaccharide polyribosylribitol phosphate, group B streptococcal polysaccharides of serotypes III and V and *Salmonella typhi* Vi polysaccharide. Other polysaccharides of pneumococcal and group B streptococcal serotypes, and meningococcal serogroups are also suitable for use herein, as are other T-independent polysaccharide and oligosaccharide antigens, for example, polysaccharides or oligosaccharides derived from group A *streptococcus*, Staphylococci, Enterococci, *Klebsiella pneumoniae, E. coli, Pseudomonas aeruginosa*, and *Bacillus anthracis*. While bacterial polysaccharides and oligosaccharides are particularly preferred, gram (−) bacterial lipopolysaccharides and lipooligosaccharides and their polysaccharide and oligosaccharide derivatives, and viral polysaccharides and oligosaccharides can also be employed.

Polysaccharides with side chain phosphorus and/or backbone phosphorus are suitable for use in preferred embodiments. The conjugation reactions of preferred embodiments are particularly well suited for use with polysaccharides having phosphorus in the backbone. Such polysaccharides are sensitive to fragmentation and degradation, so the rapidity of the conjugation reaction results in a higher quality conjugate due to the reduced time during which degradation can occur.

After completion of any pre-processing steps, the polysaccharide or oligosaccharide is subjected to an "activation" step. The term "activation" refers to a chemical treatment of the polysaccharide to provide chemical groups capable of reacting with the protein. In a particularly preferred embodiment, activation involves functionalization of the polysaccharide or oligosaccharide with hydrazide groups that are reacted with aldehyde groups on a functionalized protein. Alternatively, the polysaccharide or oligosaccharide can be functionalized with aldehyde groups, ketone groups, or cyanate groups that are reacted with hydrazide groups on a functionalized protein.

Any suitable functionalization reaction can be employed to activate the polysaccharide or oligosaccharide with hydrazide groups. A preferred functionalization reaction is reductive amination, wherein the polysaccharide or oligosaccharide is reacted with $NaIO_4$ in a periodate activation reaction to yield aldehyde groups, which are then reacted with adipic acid dihydrazide, followed by subsequent reduction with $NaBH_4$. Alternatively, a cyanylation conjugation reaction can be employed, wherein polysaccharide or oligosaccharide is reacted with cyanogens bromide or 1-cyano-4-dimethylammoniumpyridinium tetrafluoroborate to introduce a cyanate group which is subsequently reacted with adipic acid dihydrazide. A carbodiimide reaction can also be employed, wherein polysaccharide or oligosaccharide is reacted with adipic acid dihydrazide in the presence 1-[3-(dimethylamino) propyl]-3-ethyl carbodiimide hydrochloride).

Any suitable functionalization reaction can be employed to activate the polysaccharide or oligosaccharide with cyanate groups. Preferably, the polysaccharide or oligosaccharide is reacted with 1-cyano-4-dimethylammoniumpyridinium tetrafluoroborate in the presence of triethylamine.

Any suitable functionalization reaction can be employed to activate the polysaccharide or oligosaccharide with aldehyde groups. Certain polysaccharides and oligosaccharides possess terminal aldehyde groups that can participate in the conjugation reaction. If the polysaccharide or oligosaccharide is activated with aldehyde groups, a preferred reaction involves reaction with an oxidizing agent, such as $NaIO_4$. Oxidizing agents have the potential for fragmenting the polysaccharide or oligosaccharide. Undesirable fragmentation can be avoided or controlled through selection of the particular oxidizing agent and the concentration of the oxidizing agent employed. Ketone groups are also capable of reacting with hydrazide, so activated of the polysaccharide or oligosaccharide with ketone groups can be employed in certain embodiments.

A strongly buffered (at pH of from about 6.5 to about 8, with a high buffer concentration of from about 100 mM to about 200 mM) activated polysaccharide solution is preferably employed in the conjugation reaction in the form of a strongly buffered solution. Any suitable buffer can be employed, preferably a buffer such as N-(2-Hydroxyethyl) piperazine-N'-(2-ethanesulfonic acid).

The Protein

The activated polysaccharide or oligosaccharide is coupled to a protein to yield a conjugate vaccine. Suitable proteins include bacterial toxins that are immunologically effective carriers that have been rendered safe by chemical or genetic means for administration to a subject. Examples include inactivated bacterial toxins such as diphtheria toxoid, $CRM_{197}$, tetanus toxoid, pertussis toxoid, *E. coli* LT, *E. coli* ST, and exotoxin A from *Pseudomonas aeruginosa*. Bacterial outer membrane proteins such as, outer membrane complex c (OMPC), porins, transferrin binding proteins, pneumolysin, pneumococcal surface protein A (PspA), pneumococcal adhesin protein (PsaA), or pneumococcal surface proteins BVH-3 and BVH-11 can also be used. Other proteins, such as protective antigen (PA) of *Bacillus anthracis*, ovalbumin, keyhole limpet hemocyanin (KLH), human serum albumin, bovine serum albumin (BSA) and purified protein derivative of tuberculin (PPD) can also be used. The proteins are preferably proteins that are non-toxic and non-reactogenic and obtainable in sufficient amount and purity that are amenable to the conjugation methods of preferred embodiments. For example, diphtheria toxin can be purified from cultures of *Corynebacteria diphtheriae* and chemically detoxified using formaldehyde to yield a suitable protein.

Fragments of the native toxins or toxoids, which contain at least one T-cell epitope, are also useful, as are outer membrane protein complexes, as well as certain analogs, fragments, and/or analog fragments of the various proteins listed above. The proteins can be obtained from natural sources, can be produced by recombinant technology, or by synthetic methods as are known in the art. Analogs can be obtained by various means, for example, certain amino acids can be substituted for other amino acids in a protein without appreciable loss of interactive binding capacity with structures such as, for example, antigen-binding regions of antibodies or binding sites on substrate molecules. Other proteins can also be employed, such as those containing surface exposed glutamic acid or aspartic acid groups.

Any suitable functionalization reaction can be employed to activate the protein with hydrazide groups. Conventional methods for preparing hydrazide-modified proteins include EDC catalysis and a two-step process using N-succinimidyl iodoacetate and thiol hydrazide through lysine ε-amino groups of the protein. See King et al., Biochemistry 1986; 25:5774-5779. Modified protein prepared by EDC catalysis typically needs to be fractionated in order for it to be suitable for use in conjugation, and the two-step process is tedious. Accordingly, it is generally not preferred to employ such methods for preparing the hydrazide-modified protein. However, in certain embodiments such methods can be acceptable or even desirable.

Preferably, hydrazide groups are introduced into proteins through the carboxyl groups of aspartic acid and glutamic acid residues on the protein using a carbodiimide reaction, for example, by reaction with hydrazine, carbohydrazide, succinyl dihydrazide, adipic acid dihydrazide or any other dihydrazides in the presence of EDC. EDC is employed as a catalyst to activate and modify the protein reactant with hydrazine or the dihydrazide. Any water-soluble carbodiimide including EDC can be used as a catalyst. EDC-catalyzed proteins generally have a tendency to polymerize and precipitate, and thus are generally not preferred for preparation of conjugates involved with protein. See Schneerson et al., Infect. Immun. 1986; 52:519-528; Shafer et al., Vaccine 2000; 18(13): 1273-1281; and Inman et al., Biochemistry 1969; 8:4074-4082. Aggregation and precipitation of the activated protein depends, in part, on its pH environment. Accordingly, the tendency to polymerize and precipitate can be controlled by maintaining such hydrazide-modified proteins soluble in a buffered solution. By buffer-exchanging the reaction mixture so as to maintain the activated protein at a pH of about 10.5, the activated protein remains soluble and stable for conjugation. Any suitable buffer can be employed. Preferably a weak buffer such as $Na_2CO_3$ at a low concentration of from about 3 mM to about 10 mM is employed.

The buffered hydrazide-modified protein can then be employed in preparing protein-polysaccharide conjugates without precipitation when added to activated polysaccharide at a pH of from about 6 to 8.5, preferably from about 6.5 to about 8. Any suitable functionalization reaction can be employed to activate the protein with aldehyde groups. Preferably, the protein is reacted with 1-amino-2,3-propanediol in the presence of EDC. Amino sugars such as glucosamine, galactosamine, and the like can be used in place of 1-amino-2,3-propanediol. In this reaction, EDC is also employed as a catalyst to activate and modify the protein reactant with the aminodiol through the carboxyl groups of aspartic acid and glutamic acid residues of the protein.

Preparation of Conjugates by Reductive Amination

Conjugates can be prepared via the reaction of aldehyde and hydrazide groups (reductive amination). The reductive amination conjugation reaction can be employed to conjugate a hydrazide-modified reactant (protein or polysaccharide) to the other component containing aldehyde groups.

In conventional reductive amination, the reaction between aldehyde and amino groups is reversible and unfavorable, such that sodium cyanoborohydride is needed to facilitate the conjugation by converting the C=N double bond to a C—N single bond to render the entire reductive amination event irreversible. In contrast, the reductive amination conjugation reaction of preferred embodiments proceeds without the aid of sodium cyanoborohydride because of the high efficiency of the hydrazide-aldehyde reaction. At the end of the reductive amination conjugation reaction, sodium borohydride or another suitable reactant is employed to reduce the C=N double bond to a C—N single bond, as well as to reduce any residual aldehyde groups to alcohol groups. The reductive amination conjugation reaction of preferred embodiments avoids contamination of the resulting conjugate with cyanide, a by-product of sodium cyanoborohydride.

To reduce precipitation of activated protein during the conjugation reaction, the activated protein is preferably in the form of a weakly buffered solution with a low buffer concentration of from about 3 mM to about 10 mM which is added to a strongly buffered (at pH of from about 6.5 to about 7.5, with a high buffer concentration of from about 100 mM to about 200 mM) activated polysaccharide solution. Preferably, the pH of the activated protein solution is buffered to from about 10 pH to about 11.5 pH, most preferably to about 10.5 pH. The activated polysaccharide solution is preferably strongly buffered to from about 6 pH to about 8 pH, most preferably to from about 6.5 pH to about 7.5 pH. The hydrazide-aldehyde reductive amination reaction proceeds at a fast rate, and the precipitating effect of a pH lower than 10.5 (for example, a pH as low as from about 8.5 to about 9.5) on activated protein is overcome by the molecular properties of the reacting activated polysaccharide.

Preparation of Conjugates by Cyanylation Conjugation

Conjugates can be prepared via the reaction of hydrazide and cyanate groups (cyanalation conjugation). The cyanalation conjugation reaction is efficient and reversible, favoring the product formation. In certain embodiments, blocking agents are employed to remove residual cyanate groups. However, addition of a blocking agent to the reaction mixture drives the conjugation reaction backward and reduces the conjugation yield by 5-12%. The effect of various blocking agents on yield was investigated. The pneumococcal polysaccharide Pn 18C PS was activated with CDAP and then conjugated to hydrazide activated tetanus toxoid (TTH) overnight. Five aliquots were added with either water or a blocking agent to 0.2 M. After 4 hours incubation, the samples were analyzed by HPSEC using a Waters Ultrahydrogel 2000 column with a 280 nm monitor (FIG. 2). The conjugation yield of each sample, provided in Table 3, was determined as the % area of the conjugate peak at 15.5 minutes over total protein, i.e. conjugate peak plus the free TTH peak (at 22 minutes). While in certain embodiments it can be desirable to employ blocking agents to quench the leftover residual cyanate groups, it is generally preferred to avoid their use so as to avoid reduction in conjugate yield.

TABLE 3

| Blocking agent (0.2M) | Conjugation yield | % Control | % Reduction |
|---|---|---|---|
| None (control) | 75 | 100 | 0 |
| ADH | 63 | 84 | 16 |
| Hydrazine | 70 | 93 | 7 |
| Glycine | 66 | 89 | 11 |
| Ethanolamine | 65 | 87 | 13 |

To remove residual cyanate groups in the conjugation product without using a blocking agent, the conjugation time can be prolonged. Preferably, conjugation is conducted at a temperature of from about 0° C. to about 5° C. for about 36 to about 48 hours, most preferably at about 4° C. for about 36 hours, followed by about an additional 18 to 24 hours at a temperature of from about 20° C. to about 25° C., most preferably at about 18 hours at about 20 to 24° C., such that the residual cyanate groups react with water and decompose. Longer or shorter conjugation times and/or higher or lower conjugation temperatures can be employed, and different sequences of steps at various times and temperatures can be conducted, as desired. It is desirable, however, to conduct the conjugation reaction, at least initially, at low temperatures, preferably from about 0° C. to about 5° C., more preferably at about 4° C., so as to reduce the degree of precipitation of the conjugate.

With high conjugation yields and high immunogenicity of the conjugation product, purification processes such as column chromatography and/or ammonium sulfate precipitation of the conjugate from unconjugated polysaccharide may not be necessary. However, in certain embodiments it can be desirable to conduct one or more purification steps.

The Conjugates

Both reactants contain multiple reactive groups per molecule. An activated polysaccharide molecule can react with and form more than one linkage to more than one activated protein molecule. Likewise, an activated protein molecule can react with and form more than one linkage to more than one activated polysaccharide molecule. Therefore, the conjugate product is a mixture of various crosslinked matrix-type lattice structures. For example, a single linkage can be present, or 2, 3, 4, 5, 6, 7, 8, 9, 10, 11, 12, 13, 14, 15, 16, 17, 18, 19, 20, 21, 22, 23, 24, 25, 26, 27, 28, 29, or 30 or more linkages can be present. The average number of linkages between a polysaccharide and a protein can be adjusted, as preferred. The preferred average number of linkages can depend upon the type of polysaccharide, the type of protein, the conjugation method, the reaction conditions, and the like. Generally, an average of 1 linkage to about 2, 3, 4, or 5 linkages is present, so as to avoid interfering with the ability of the protein to stimulate the immune system by over-conjugation, and so as to not cause changes in the polysaccharide structure. However, in certain embodiments more than 5 linkages can be tolerated or even desirable.

After conjugation, the conjugate can be purified by any suitable method. Purification is employed to remove unreacted polysaccharide, protein, or small molecule reaction byproducts. Purification methods include ultrafiltration, size exclusion chromatography, density gradient centrifugation, hydrophobic interaction chromatography, ammonium sulfate fractionation, and the like, as are known in the art. As discussed above, the conjugation reactions of preferred embodiments proceed with higher yield, and generate fewer undesirable small molecule reaction byproducts. Accordingly, no purification may be necessary, or only a minor degree of purification can be desirable. The conjugate can be concentrated or diluted, or processed into any suitable form for use in pharmaceutical compositions, as desired.

Methods of Treatment

Conjugates prepared according to the preferred embodiment are administered to a subject in an immunologically effective dose in a suitable form to treat and/or prevent infectious diseases. The term "subject" as used herein, refers to animals, such as mammals. For example, mammals contemplated include humans, primates, dogs, cats, sheep, cattle, goats, pigs, horses, mice, rats, rabbits, guinea pigs, and the like. The terms "subject", "patient", and "host" are used interchangeably. As used herein, an "immunologically effective" dose of the conjugate vaccine is a dose which is suitable to elicit an immune response. The particular dosage depends upon the age, weight and medical condition of the subject to be treated, as well as on the method of administration. Suitable doses can be readily determined by those of skill in the art.

Pharmaceutical compositions comprising conjugate vaccines of preferred embodiments can offer various advantages over conventional vaccines, including enhanced immunogenicity of weakly immunogenic antigens, potential reduction in the amount of antigen used, less frequent booster immunizations, improved efficacy, preferential stimulation of immunity, or potential targeting of immune responses. The vaccines can be administered to a subject by a variety of routes, as discussed below, including but not limited to parenteral (e.g., by intracisternal injection and infusion techniques), intradermal, transmembranal, transdermal (including topical), intramuscular, intraperitoneal, intravenous, intra-arterial, intralesional, subcutaneous, oral, and intranasal (e.g., inhalation) routes of administration. Conjugate vaccine can be administered by bolus injection or by continuous infusion, as well as by localized administration, e.g., at a site of disease or injury. The conjugate vaccine can be optionally administered in a pharmaceutically or physiologically acceptable vehicle.

The term "vaccine" as used herein, is a broad tem and is used in its ordinary sense, including, without limitation, conjugates of preferred embodiments or other antigens formulated with adjuvants, diluents, excipients, carriers, and other pharmaceutically acceptable substances. The term "pharmaceutically acceptable" is used to refer to a non-toxic material that is compatible with a biological system such as a cell, cell culture, tissue, or organism.

Immunization protocols for use with the conjugates of preferred embodiments provide compositions and methods for preventing or treating a disease, disorder and/or infection in a subject. The term "treating" as used herein, is a broad term and is used in its ordinary sense, including, without limitation, curative, preventative, prophylactic, palliative and/or ameliorative treatment.

The vaccine compositions are preferably sterile and contain either a therapeutically or prophylactically effective amount of the conjugate in a unit of weight or volume suitable for administration to a subject. The term "pharmaceutically-acceptable carrier" as used herein means one or more compatible solid or liquid filler, diluents or encapsulating substances which are suitable for administration into a subject. The term "carrier" denotes an organic or inorganic ingredient, natural or synthetic, with which the active ingredient is combined to facilitate the application. The characteristics of the carrier depend on the route of administration. Physiologically and pharmaceutically-acceptable carriers include diluents, fillers, salts, buffers, stabilizers, solubilizers, and other materials which are well known in the art.

The components of the pharmaceutical compositions also are capable of being co-mingled with the conjugates of the preferred embodiment, and with each other, in a manner such that there is no interaction which substantially impairs the desired pharmaceutical efficacy.

Formulation of the conjugate vaccines of preferred embodiments into pharmaceutical compositions can be accomplished using methods known in the art. The vaccine compositions can also contain one or more adjuvants. Suitable adjuvants include, for example, aluminum adjuvants, such as aluminum hydroxide or aluminum phosphate, Freund's Adjuvant, BAY, DC-chol, pcpp, monophoshoryl lipid A, CpG, QS-21, cholera toxin and formyl methionyl peptide. See, e.g., Vaccine Design, the Subunit and Adjuvant Approach, 1995 (M. F. Powell and M. J. Newman, eds., Plenum Press, N.Y.).

The dosage of conjugate vaccine to be administered a subject and the regime of administration can be determined in accordance with standard techniques well known to those of ordinary skill in the pharmaceutical and veterinary arts, taking into consideration such factors as the intended use, particular antigen, the adjuvant (if present), the age, sex, weight, species, general condition, prior illness and/or treatments, and the route of administration. Preliminary doses can be determined according to animal tests, and the scaling of dosages for human administration is performed according to art-accepted practices such as standard dosing trials. For example, the therapeutically effective dose can be estimated initially from serum antibody level testing. The dosage depends on the specific activity of the conjugate and can be readily determined by routine experimentation.

In practicing immunization protocols for treatment and/or prevention of specified diseases, a therapeutically effective amount of conjugate is administered to a subject. As used herein, the term "effective amount" means the total amount of therapeutic agent (e.g., conjugate) or other active component that is sufficient to show a meaningful benefit to the subject, such as, enhanced immune response, treatment, healing, prevention or amelioration of the relevant medical condition (disease, infection, or the like), or an increase in rate of treatment, healing, prevention or amelioration of such conditions. When "effective amount" is applied to an individual therapeutic agent administered alone, the term refers to that therapeutic agent alone. When applied to a combination, the term refers to combined amounts of the ingredients that result in the therapeutic effect, whether administered in combination, serially or simultaneously. As used herein, the phrase "administering an effective amount" of a therapeutic agent means that the subject is treated with said therapeutic agent(s) in an amount and for a time sufficient to induce an improvement, and preferably a sustained improvement, in at least one indicator that reflects the severity of the disease, infection, or disorder.

An improvement is considered "sustained" if the patient exhibits the improvement on at least two occasions separated by a period of time. The degree of improvement can be determined based, for example, on immunological data, or on signs or symptoms of a disease, infection, or disorder. Various indicators that reflect the extent of the patient's illness can be assessed for determining whether the amount and time of the treatment is sufficient. The baseline value for the chosen indicator or indicators can established based on by examination of the patient prior to administration of the first dose of the therapeutic agent, or based on statistical values generated from a population of healthy patients. If the therapeutic agent is administered to treat acute symptoms, the first dose is administered as soon as practically possible. Improvement is induced by administering therapeutic agents until the subject manifests an improvement over baseline for the chosen indicator or indicators. In treating chronic conditions, this degree of improvement is obtained by repeatedly administering the therapeutic agents over a period time, e.g., for one, two, or three months or longer, or indefinitely. A single dose can be sufficient for treating or preventing certain conditions. Treatment can be continued indefinitely at the same level or at a reduced dose or frequency, regardless of the patient's condition, if desired. Once treatment has been reduced or discontinued, it later can be resumed at the original level if symptoms reappear.

Generally, the amount of conjugate that provides an efficacious dose or therapeutically effective dose for vaccination against bacterial infection is from about 1 µg or less to about 100 µg or more, preferably from about 2, 3, 4, 5, 6, 7, 8, 9, 10, 15, 20, 25, 30, 35, 40, 45 or 50 µg to about 55, 60, 65, 70, 75, 80, 85, 90, or 95 µg per kg body weight. An efficacious dosage can require less antibody if the post-infection time elapsed is less, since there is less time for the bacteria to proliferate. An efficacious dosage can also depend on the bacterial load at the time of diagnosis. Multiple injections administered over a period of days can be considered for therapeutic usage.

The conjugate vaccines can be administered as a single dose or in a series including one or more boosters. For example, an infant or child can receive a single dose early in life, then be administered a booster dose up to 1, 2, 3, 4, 5, 6, 7, 8, 9, 10 or more years later. The booster dose generates antibodies from primed B-cells, i.e., an anamnestic response. That is, the conjugate vaccine elicits a high primary functional antibody response in infants or children, and is capable of eliciting an anamnestic response following a booster administration, demonstrating that the protective immune response elicited by the conjugate vaccine is long-lived.

The conjugate vaccines can be formulated into liquid preparations for, e.g., oral, nasal, anal, rectal, buccal, vaginal, peroral, intragastric, mucosal, perlingual, alveolar, gingival, olfactory, or respiratory mucosa administration. Suitable forms for such administration include suspensions, syrups, and elixirs. The conjugate vaccines can also be formulated for parenteral, subcutaneous, intradermal, intramuscular, intraperitoneal or intravenous administration, injectable administration, sustained release from implants, or administration by eye drops. Suitable forms for such administration include sterile suspensions and emulsions. Such conjugate vaccines can be in admixture with a suitable carrier, diluent, or excipient such as sterile water, physiological saline, glucose, and the like. The conjugate vaccines can also be lyophilized. The conjugate vaccines can contain auxiliary substances such as wetting or emulsifying agents, pH buffering agents, gelling or viscosity enhancing additives, preservatives, flavoring agents, colors, and the like, depending upon the route of administration and the preparation desired. Standard texts, such as "Remington: The Science and Practice of Pharmacy", Lippincott Williams & Wilkins; 20th edition (Jun. 1, 2003) and "Remington's Pharmaceutical Sciences", Mack Pub. Co.; 18$^{th}$ and 19$^{th}$ editions (December 1985, and June 1990, respectively), incorporated herein by reference in their entirety, can be consulted to prepare suitable preparations, without undue experimentation. Such preparations can include complexing agents, metal ions, polymeric compounds such as polyacetic acid, polyglycolic acid, hydrogels, dextran, and the like, liposomes, microemulsions, micelles, unilamellar or multilamellar vesicles, erythrocyte ghosts or spheroblasts. Suitable lipids for liposomal formulation include, without limitation, monoglycerides, diglycerides, sulfatides, lysolecithin, phospholipids, saponin, bile acids, and the like. The presence of such additional components can influence the physical state, solubility, stability, rate of in vivo release, and rate of in vivo clearance, and are thus chosen according to the intended application, such that the characteristics of the carrier are tailored to the selected route of administration.

The conjugate vaccines are preferably provided as liquid suspensions or as freeze-dried products. Suitable liquid preparations include, e.g., isotonic aqueous solutions, suspensions, emulsions, or viscous compositions that are buffered to a selected pH. Transdermal preparations include lotions, gels, sprays, ointments or other suitable techniques. If nasal or respiratory (mucosal) administration is desired (e.g., aerosol inhalation or insufflation), compositions can be in a form and dispensed by a squeeze spray dispenser, pump dispenser or aerosol dispenser. Aerosols are usually underpressure by means of a hydrocarbon. Pump dispensers can preferably dispense a metered dose or a dose having a particular particle size, as discussed below.

When in the form of solutions, suspensions and gels, formulations of the conjugate can typically contain a major amount of water (preferably purified water) in addition to the active ingredient. Minor amounts of other ingredients such as pH adjusters, emulsifiers, dispersing agents, buffering agents, preservatives, wetting agents, jelling agents, colors, and the like can also be present.

The compositions are preferably isotonic with the blood or other body fluid of the recipient. The isotonicity of the compositions can be attained using sodium tartrate, propylene glycol or other inorganic or organic solutes. Sodium chloride is particularly preferred. Buffering agents can be employed, such as acetic acid and salts, citric acid and salts, boric acid and salts, and phosphoric acid and salts. Parenteral vehicles include sodium chloride solution, Ringer's dextrose, dextrose and sodium chloride, lactated Ringer's or fixed oils. Intravenous vehicles include fluid and nutrient replenishers, electrolyte replenishers (such as those based on Ringer's dextrose), and the like.

Viscosity of the compositions can be maintained at the selected level using a pharmaceutically acceptable thickening agent. Methylcellulose is preferred because it is readily and economically available and is easy to work with. Other suitable thickening agents include, for example, xanthan gum, carboxymethyl cellulose, hydroxypropyl cellulose, carbomer, and the like. The preferred concentration of the thickener can depend upon the agent selected. The important point is to use an amount that can achieve the selected viscosity. Viscous compositions are normally prepared from solutions by the addition of such thickening agents.

A pharmaceutically acceptable preservative can be employed to increase the shelf life of the compositions. Benzyl alcohol can be suitable, although a variety of preservatives including, for example, parabens, thimerosal, chlorobutanol, or benzalkonium chloride can also be employed. A suitable concentration of the preservative can be from 0.02% to 2% based on the total weight although there can be appreciable variation depending upon the agent selected.

Pulmonary delivery of the conjugate can also be employed. The conjugate is delivered to the lungs of a mammal while inhaling and traverses across the lung epithelial lining to the blood stream. A wide range of mechanical devices designed for pulmonary delivery of therapeutic products can be employed, including but not limited to nebulizers, metered dose inhalers, and powder inhalers, all of which are familiar to those skilled in the art. These devices employ formulations suitable for the dispensing of the conjugate. Typically, each formulation is specific to the type of device employed and can involve the use of an appropriate propellant material, in addition to diluents, adjuvants and/or carriers useful in therapy.

The conjugate is advantageously prepared for pulmonary delivery in particulate form with an average particle size of from 0.1 um or less to 10 urn or more, more preferably from about 0.2, 0.3, 0.4, 0.5, 0.6, 0.7, 0.8, or 0.9 μm to about 1.0, 1.5, 2.0, 2.5, 3.0, 3.5, 4.0, 4.5, 5.0, 5.5, 6.0, 6.5, 7.0, 7.5, 8.0, 8.5, 9.0, or 9.5 μm for pulmonary delivery. Pharmaceutically acceptable carriers for pulmonary delivery of the conjugates include carbohydrates such as trehalose, mannitol, xylitol, sucrose, lactose, and sorbitol. Other ingredients for use in formulations can include DPPC, DOPE, DSPC and DOPC. Natural or synthetic surfactants can be used, including polyethylene glycol and dextrans, such as cyclodextran. Bile salts and other related enhancers, as well as cellulose and cellulose derivatives, and amino acids can also be used. Liposomes, microcapsules, microspheres, inclusion complexes, and other types of carriers can also be employed.

Formulations suitable for use with a nebulizer, either jet or ultrasonic, typically comprise the conjugate dissolved or suspended in water at a concentration of about 0.01 or less to 100 mg or more of conjugate per mL of solution, preferably from about 0.1, 1, 2, 3, 4, 5, 6, 7, 8, 9, or 10 mg to about 15, 20, 25, 30, 35, 40, 45, 50, 55, 60, 65, 70, 75, 80, 85, or 90 mg of conjugate per mL of solution. The formulation can also include a buffer and a simple sugar (e.g., for protein stabilization and regulation of osmotic pressure). The nebulizer formulation can also contain a surfactant, to reduce or prevent surface induced aggregation of the conjugate caused by atomization of the solution in forming the aerosol.

Formulations for use with a metered-dose inhaler device generally comprise a finely divided powder containing the inventive compound suspended in a propellant with the aid of a surfactant. The propellant can include conventional propellants, such chlorofluorocarbon, a hydrochlorofluorocarbons, hydrofluorocarbons, and hydrocarbons, such as trichlorofluoromethane, dichlorodifluoromethane, dichlorotetrafluoroethanol, and 1,1,1,2-tetrafluoroethane, and combinations thereof. Suitable surfactants include sorbitan trioleate, soya lecithin, and oleic acid.

Formulations for dispensing from a powder inhaler device typically comprise a finely divided dry powder containing the conjugate, optionally including a bulking agent, such as lactose, sorbitol, sucrose, mannitol, trehalose, or xylitol in an amount that facilitates dispersal of the powder from the device, typically from about 1 wt. % or less to 99 wt. % or more of the formulation, preferably from about 5, 10, 15, 20, 25, 30, 35, 40, 45, or 50 wt. % to about 55, 60, 65, 70, 75, 80, 85, or 90 wt. % of the formulation.

When the conjugate is administered by intravenous, cutaneous, subcutaneous, or other injection, the conjugate vaccine is preferably in the form of a pyrogen-free, parenterally acceptable aqueous solution. The preparation of parenterally acceptable solutions with suitable pH, isotonicity, stability, and the like, is within the skill in the art. A preferred pharmaceutical composition for injection preferably contains an isotonic vehicle such as Sodium Chloride Injection, Ringer's Injection, Dextrose Injection, Dextrose and Sodium Chloride Injection, Lactated Ringer's Injection, or other vehicles as are known in the art. The pharmaceutical compositions can also contain stabilizers, preservatives, buffers, antioxidants, or other additives known to those of skill in the art.

The duration of the injection can vary depending upon various factors, and can comprise a single injection administered over the course of a few seconds or less, to 1, 2, 3, 4, 5, 6, 7, 8, 9, 10, 11, 12, 13, 14, 15, 16, 17, 18, 19, 20, 21, 22, 23, or 24 hours or more of continuous intravenous administration.

The conjugate can be administered topically, systematically, or locally, via a liquid or gel, or as an implant or device The conjugates of preferred embodiments, or the conjugation methods of preferred embodiments, can be useful in preparing vaccines for the treatment of a variety of bacterial infections, including infections by *Helicobacter pyloris, Dorelia burgdorferi, Legionella pneumophilia, Mycobacteria* sps. (e.g. *M. tuberculosis, M. avium, M. intracellular, M. kansaii, M. gordonae*), *Staphylococcus aureus. Neisseria gonorrhoeae, Neisseria meningitidis, Listeria monocytogenes, Streptococcus pyogenes* (Group A *Streptococcus*), *Streptococcus agalactiae* (Group B *Streptococcus*), *Streptococcus* (*viridans* group), *Streptococcus faecalis, Streptococcus bovis, Streptococcus* (*anaerobic* sps.), *Streptococcus pneumoniae*, pathogenic *Campylobacter* sp., *Enterococcus* sp., *Haemophilus influenzae, Bacillus anthracia, Corynebacterium diphtheriae, corynebacterium* sp., *Erysipelothrix rhusiopathiae, Clostridium perfringens, Clostridium tetani, Enterobacter aerogenes, Klebsiella pneumoniae, Pasturella multocida, Bacteroides* sp., *Fusobacterium nucleatum, Streptobacillus moniliformis, Treponema pallidium, Treponema pertenue, Leptospira,* and *Actinomyces israelii.*

Certain methods of the preferred embodiments can also be of use in preparing vaccines for treating or vaccinating subjects against cancer, such as mammalian sarcomas and carcinomas, such as fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, serminoma, embryonal carcinoma, Wilms' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, retinoblastoma; leukemias, such as acute lymphocytic leukemia and acute myelocytic leukemia (myeloblasts, promyelocytic, myelomonocytic, monocytic and erythroleukemia); chronic leukemia (chronic myelocytic (granulocytic) leukemia and chronic lymphocytic leukemia); and polycythemia vera, lymphoma (Hodgkin's disease and non-Hodgkin's disease), multiple myeloma, Waldenstrom's macroglobulinemia, and heavy chain disease, lymphoproliferative disorders including autoimmune lymphoproliferative syndrome (ALPS), chronic lymphoblastic leukemia, hairy cell leukemia, chronic lymphatic leukemia, peripheral T-cell lymphoma, small lymphocytic lymphoma, mantle cell lymphoma, follicular lymphoma, Burkitt's lymphoma, Epstein-Barr virus-positive T cell lymphoma, histiocytic lymphoma, Hodgkin's disease, diffuse aggressive lymphoma, acute lymphatic leukemias, T gamma lymphoproliferative disease, cutaneous B cell lymphoma, cutaneous T cell lymphoma (i.e., mycosis fungoides) and Szary syndrome.

The conjugates can be administered in combination with various vaccines either currently being used or in development, whether intended for human or non-human subjects. Examples of vaccines for human subjects and directed to infectious diseases include the combined diphtheria and tetanus toxoids vaccine; pertussis whole cell vaccine; the inactivated influenza vaccine; the 23-valent pneumococcal vaccine; the live measles vaccine; the live mumps vaccine; live rubella vaccine; Bacille Calmette-Guerin (BCG) tuberculosis vaccine; hepatitis A vaccine; hepatitis B vaccine; hepatitis C vaccine; rabies vaccine (e.g., human diploid cell vaccine); inactivated polio vaccine; meningococcal polysaccharide vaccine; quadrivalent meningococcal vaccine; yellow fever live virus vaccine; typhoid killed whole cell vaccine; cholera vaccine; Japanese B encephalitis killed virus vaccine; adenovirus vaccine; cytomegalovirus vaccine; rotavirus vaccine; varicella vaccine; anthrax vaccine; small pox vaccine; and other commercially available and experimental vaccines.

The conjugates can be provided to an administering physician or other health care professional in the form of a kit. The kit is a package which houses a container which contains the conjugate vaccine and instructions for administering the conjugate vaccine to a subject. The kit can optionally also contain one or more other therapeutic agents. The kit can optionally contain one or more diagnostic tools and instructions for use. For example, a vaccine cocktail containing two or more vaccines can be included, or separate pharmaceutical compositions containing different vaccines or therapeutic agents. The kit can also contain separate doses of the conjugate vaccine for serial or sequential administration. The kit can contain suitable delivery devices, e.g., syringes, inhalation devices, and the like, along with instructions for administrating the therapeutic agents. The kit can optionally contain instructions for storage, reconstitution (if applicable), and administration of any or all therapeutic agents included. The kits can include a plurality of containers reflecting the number of administrations to be given to a subject. If the kit contains a first and second container, then a plurality of these can be present.

EXPERIMENTS

Materials

Tetanus toxoid (TT) was obtained from Lederle Vaccines, Pearl River, N.Y. and Serum Institute of India, Pune, India. Meningococcal groups A and C polysaccharides (Mn A PS and Mn C PS, respectively) were obtained from Bio-Manguinhos, Rio de Janeiro, Brazil. Mn A PS was also obtained from SynCo Bio Partners, Amsterdam, The Netherlands. Mn W135 and Y PS's were obtained from Aventis Pasteur. PSs of Pneumococcus (Pn) serotypes 1, 2, 3, 4, 5, 6B, 7F, 8, 9N, 9V, 10A, 11 A, 12F, 14, 15B, 17F, 18C, 19A, 19F, 20, 22F, 23F and 33F were obtained from Lederle Vaccines. PS of *Hemophilus influenzae* type b (PRP or Hib PS) was obtained from Lederle Vaccines. Vi PS of *Salmonnella typhi* was obtained from Aventis Pasteur. PSs of group B *streptococcus* serotypes III and V were isolated from culture media according to the published protocol. See Carey et al. Infection and Immunity 1980; 28:195-203. Hydrazine, carbohydrazide, adipic acid dihydrazide (ADH), 1-[3-(dimethylamino) propyl]-3-ethyl carbodiimide hydrochloride (EDC), N-(2-Hydroxyethyl)piperazine-N'-(2-ethanesulfonic acid) (HEPES), sodium periodate, sodium borohydride, sodium cynoborohydride, 4-cyno-dimethylamino pyridium tetrafluoroborate (CDAP), and 1-amino-2,3-propanediol were purchased from Sigma/Aldrich Chemical Company. TNBSA (2,4,6-trinitrobenzene-sulfonic acid) and BCA (bicinchoninic acid) assay kit were purchased from Pierce.

Methods

The bacterial polysaccharides used for conjugation to protein by the methods described herein include Meningococcal serogroups A, C, W135 and Y polysaccharides, Pneumococcus serotypes 1, 2, 3, 4, 5, 6B, 7F, 8, 9N, 9V, 10A, 11A, 12F, 14, 15B, 17F, 18C, 19A, 19F, 20, 22F, 23F and 33F polysaccharides, *Hemophilus influenzae* type b polysaccharide (PRP or Hib PS), Vi polysaccharide of *Salmonnella typhi* and group B *Streptococcus* serotypes III and V polysaccharides. Three general methods are described for conjugating polysaccharides to protein, referred to below as General Method A, General Method B, and General Method C.

General Method A: Aldehyde-Activated PS to Hydrazide-Activated Protein (Reductive Amination Conjugation)

Tetanus toxoid is activated with hydrazine or adipic acid dihydrazide in the presence of EDC at pH 6.5 and then buffer exchanged with 30 mM NaCl, 3 mM $Na_2CO_3$, pH about 10.5. Polysaccharide is activated with $NaIO_4$, and buffer exchanged with 10 mM HEPES, pH 7.5, 4° C. Hydrazide-activated TT is reacted with aldehyde-activated polysaccharide at ratios from 2:1 to 1:2 and concentration range of 1-40 mg/mL overnight, pH 6.5-7.5, 4-40° C. $NaBH_4$ (ten-fold moles of the aldehyde groups in the initial reactant) is then added for 6 hrs to reduce the C=N double bond to C—N single bond and also reduce the unreacted aldehyde groups to alcohol. The solution is buffer-exchanged with saline, 10 mM HEPES, pH 7.5, 1 mM EDTA using a 12-14 KDa molecular weight cut-off membrane. The total protein content is determined by Lowry assay (see Pierce Catalog 2003-2004, page 306). Total polysaccharide content is determined by various chemical assays for different bacterial polysaccharides, e.g. resorcinol assay for Mn A and C PSs (Monsigny et al., Anal. Biochem. 1988; 175:525-530), anthrone assay for Pn PSs (Keleti et al., Handbook of micromethods for the biological sciences. 61. Hexoses (Anthrone). Page 73. Van Nostrand Reinhold Co., New York, 1974), phosphorus assay for Mn A PS, Hib PS and phosphorus-containing Pn PS, and purpald assay for Mn W135 and Y PSs and glycol-containing Pn PSs (Lee et al., Anal. Biochem. 2001; 296:73-82).

General Method B: Cyanate-Activated PS to Hydrazide-Activated Protein (Cyanylation Conjugation)

Tetanus toxoid is activated with hydrazine or adipic acid dihydrazide in the presence of EDC at pH 6.5 and then buffer exchanged with 30 mM NaCl, 3 mM $Na_2CO_3$, pH about 10.5. Polysaccharide is activated with CDAP for 2-2.5 minutes at 20-24° C. in the presence of triethylamine. At 4° C., hydrazide-activated TT is reacted with cyanate-activated polysaccharide at ratios from 2:1 to 1:2 and concentration range of 0.2-1 mg/mL, pH 6.5-7.5. After reaction for 36 hours at 4° C., the mixture is incubated at 20-24° C. for another 18 hours. The prolonged incubation is to ensure decomposition of the residual leftover unreacted cyanate groups. The solution is buffer-exchanged with saline, 10 mM HEPES, pH 7.5, 1 mM EDTA using a 12-14 KDa molecular weight cut-off membrane. The total protein content is determined by Lowry assay, as noted above in reference to General Method A. Total polysaccharide content is determined by various chemical assays for different bacterial polysaccharides, e.g., resorcinol assay for Mn A and C PSs, anthrone assay for Pn PSs, phosphorus assay for Mn A PS, Hib PS and phosphorus-containing Pn PS, and purpald assay for Mn W135 and Y PSs and glycol-containing Pn PSs, as noted above in reference to General Method A.

General Method C: Hydrazide-Activated PS to Aldehyde-Activated Protein (Reductive Amination Conjugation)

Tetanus toxoid is reacted with 1-amino-2,3-propanediol (APDO) in the presence of EDC at pH 6.5 and then buffer-exchanged with 30 mM NaCl, 3 mM $Na_2CO_3$, pH about 10.5. TT-APDO is reacted with $NaIO_4$ to create aldehyde groups and then buffer exchanged with 30 mM NaCl, 3 mM $Na_2CO_3$, pH about 10.5. Three methods used to prepare hydrazide-activated polysaccharide: a) PS is reacted with $NaIO_4$ and then adipic acid dihydrazide with subsequent reduction with $NaBH_4$ (reductive amination); b) PS is activated with CDAP and then reacts with adipic acid dihydrazide (cyanylation conjugation reaction); or c) Ps is reacted with adipic acid dihydrazide in the presence EDC (carbodiimide reaction). Aldehyde-activated TT is reacted with hydrazide-activated PS at ratio from 2:1 to 1:2 and concentration range 1-5 mg/mL for 18 hours, pH 6.5-7.5, 4-40° C. $NaBH_4$; (ten-fold moles of the aldehyde in the initial reactant) is then added for 6 hrs to reduce the C=N double bond to C—N single bond and also reduce the unreacted aldehyde groups to alcohol. The solution is buffer-exchanged with saline, 10 mM HEPES, pH 7.5, 1 mM EDTA using a 12-14 KDa molecular weight cut-off membrane. The total protein content is determined by Lowry assay, as noted above in reference to General Method A. Total polysaccharide content is determined by various chemical assays for different bacterial polysaccharides, e.g., resorcinol assay for Mn A and C PSs, anthrone assay for Pn PSs, phosphorus assay for Mn A PS, Hib PS and phosphorus-containing Pn PS, and purpald assay for Mn W135 and Y PSs and glycol-containing Pn PSs, as noted above in reference to General Method A.

Physico-Chemical Assays of Reactants. Activated PS and Conjugate Products

High Performance Liquid Size-Exclusion Chromatography (HPSEC)

Samples of proteins, polysaccharides and conjugate products (25 µL, 0.01-1 mg/mL) were run through a Waters Ultrahydrogel 2000 or Ultrahydrogel Linear column with saline at 0.5 mL/minute in a Dionex HPLC system using Chromclean software, a UV detector at 280 and 206 nm and a Waters 2410 differential refractometer (RI detector). The UV detector at 280 nm monitored the signals of protein-containing species as well as compounds containing aromatic moieties. The UV detector at 206 nm detected the protein and PS by presence of carbonyl groups, while the RI detector measured the signals of proteins, polysaccharides, conjugates and salts.

Immunoecnicity of Polysaccharide-Protein Conjugates in Mice

Immunization of Mice

Mice (NIH-Swiss; groups of 10) were immunized with 1 µg/dose of polysaccharide or polysaccharide-protein conjugate prepared by General Method A (Mn A PS-TT and Mn C PS-TT conjugates), B (Pn 6B PS-TT and Pn 7F PS-TT conjugates) and General Method C (Pn 9V PS-TT conjugate) on days 0 and 14, or on days 0, 14 and 28, with antisera collected on day 28 and 42, respectively. ELISA was carried out for determination of antibody levels against respective native polysaccharides.

ELISA Method

Immunolon 1 plates (Dynatech) were coated with 100 µL coating solution containing polysaccharide (5 µg/mL for Mn A and C, and Pn 7F PS's; 2 µg/mL for Pn 6B PS; and 2.5 µg/mL for Pn 9V PS) admixed with methylated human serum albumin (5 μg/mL for Mn A and C, and Pn 6B and 7F PS's; and 2.5 μg/mL for Pn 9V PS) for 18 hours. After washing three times with 1504 washing buffer (PBS with 0.05% Tween 20, 0.02% NaN₃), 100 μL of specific anti-serum samples and reference serum (with assigned 3200 units/mL anti-polysaccharide antibody; duplicate) at a serial two-fold dilution starting from 1/200 (diluted with dilution buffer containing PBS, 4% newborn calf serum, 0.02% NaN₃ (with 2 μg/mL cell wall polysaccharide in pneumococcal cases)), was added to each well. After overnight incubation, the plates were washed three times and incubated with 100 μL goat anti-mouse IgG Fc conjugated with alkaline phosphate (1/3000 dilution in dilution buffer) for two hours. After washing (3×150 μL) the plates were incubated with 100 μL p-nitrophenyl phosphate (1 mg/mL in 1 M Tris, pH 9.8, 0.3 mM $MgCl_2$) for 30 minutes and the reaction was stopped by 50 μL 1 N NaOH. The ELISA readings were measured with a plate reader and the anti-polysaccharide antibody levels of the antiserum samples were calculated from the ELISA readings and the standard curve of the reference serum co-assayed in the same plate. The geometric mean of antibody level for each mouse group was calculated.

Specific Examples

Method A—Meningococcus Group C Conjugate

Activation of TT to Contain Hydrazide Groups

Tetanus toxoid (4.2 mg/mL) was activated with 0.42 M hydrazine or adipic acid dihydrazide in the presence of 20 mM EDC, 0.1 M MES, pH 6.5 at 20-24° C. After reacting for 4 hours, the pH of the reaction mixture was raised to 7.5-10 with 1 N NaOH to stop the reaction. The reaction mixture was buffer-exchanged with 30 mM NaCl, 3 mM $Na_2CO_3$, pH about 10.5 at 4° C. using a 12-14 KDa dialysis membrane. The protein concentration of the resulting TT-hydrazide sample was determined by Lowry assay (see Pierce Catalog 2003-2004, page 306) using bovine serum albumin as a standard. The hydrazide content was determined by TNBS assay using adipic acid dihydrazide as a standard, as described in Vidal, J. Immunol. Methods 1986; 86:155-156. The degree of activation of TT so prepared was approximately 50 hydrazide groups per TT molecule.

Activation of Mn C PS to Contain Aldehyde Groups

Mn C PS (10 mg/mL) was reacted with 6 mM $NaIO_4$ at 20-24° C. for 4 hours. The sample was dialyzed against 10 mM HEPES, pH 7.5 at 4° C. using a 12-14 KDa dialysis membrane. The concentration of the resulting activated PS was determined by resorcinol assay using N-acetyl neuraminic acid as the standard with a correction factor of Mn C PS/N-acetyl neuraminic acid=1.104/1, as described in Monsigny et al., Anal. Biochem. 1988; 175:525-530. The aldehyde content of the activated PS was determined by BCA (Pierce Catalog 2003-2004, pages 241 and 305) assay using glucose as a standard. The degree of activation of the activated Mn C PS prepared by this protocol was approximately one aldehyde group per 80 monomers.

Conjugation of Activated Mn C PS to Activated TT

An aliquot of hydrazide-containing TT was adjusted to 25 mg/mL by lyophilization and dissolution in water. An aliquot of aldehyde-containing Mn CPS was adjusted to 25 mg/mL by lyophilization and dissolution in 0.2 M HEPES, pH 7.5, 30 mM EDTA. The activated TT solution was added to an equal volume of the activated Mn C PS and vortexed. The reaction mixture was incubated at 20-24° C. for 18 hours. The reaction mixture was treated with $NaBH_4$ (10-fold molar equivalent to initial aldehyde concentration in the activated PS) for 6 hours.

The solution was buffer-exchanged with saline, 10 mM HEPES, pH 7.5, 1 mM EDTA using a 12-14 KDa molecular weight cut-off membrane. Total protein was determined by Lowry assay using bovine serum albumin as a standard. Total Mn C PS content was determined by resorcinol assay using N-acetyl neuraminic acid as a standard, as described in Monsigny et al., Anal. Biochem. 1988; 175:525-530.

Four Mn C PS-TT conjugates were prepared using hydrazine or adipic acid dihydrazide as a spacer. FIG. 3 shows the HPSEC elution profiles (monitored at 280 nm) of these conjugates. A slight shift among the profiles and a right shoulder at 22.5-25 minutes of unconjugated free protein were observed.

The unconjugated free Mn C PS was determined by the method of C18 particle absorption of protein in the conjugate product followed by comparing the saccharide signal of the supernatant in HPSEC to those of the activated Mn C PS of known concentrations (FIGS. 4 and 5). To estimate the yield of the conjugation reaction, the conjugate product was diluted to approximately 1 mg/mL concentration of Mn C PS. 100 μL of this solution was mixed and incubated with 250 μL of activated C18 particles for an hour with gentle agitation. The supernatant was collected after centrifugation, and the C18 gel was washed twice with 100 μL saline. The combined supernatant and wash was adjusted to 333 μL with saline and passed through a 0.2 um membrane microfilter. The filtrate was analyzed with HPSEC together with standard concentrations of activated Mn C PS at 0.033, 0.067 and 0.134 mg/mL, giving the area of the saccharide signals of these samples as 19.4, 4.8, 9.2, and 18.4, respectively. The saccharide concentration of the filtrate was calculated from the standard curve as 0.141 mg/mL, which was 3.3 times volume of the starting sample. Thus the starting sample contained 0.465 mg/mL (0.141 mg/mL×3.3) free Mn C PS. The total Mn C PS concentration was determined as 1.131 mg/mL by modified resorcinol assay. The yield was estimated to be about 60% (100%×(1−0.465/1.131)).

Immunogenicity of Mn C PS-TT Conjugates

The conjugates prepared as described above were used to immunize groups of 10 mice with native polysaccharide as a control at 1 μg polysaccharide/dose on days 0 and 14. The geometric means of the induced antibody levels (units/mL) two weeks post $2^{nd}$ injection were 16 (8, 34; 1 SD confidence interval) for control group and 2141 (1069, 4285), 4228 (2189, 8167), 1092 (655, 1820) and 3977 (2423, 6526) for the four conjugate batches made by Method A, assuming 3200 units/mL for the reference serum (Table 4). The conjugates induced 68-264 fold more anti-Mn C PS specific antibody in mice as compared to the native Mn C PS control.

TABLE 4

| Mouse groups of different conjugate and polysaccharide immunogens | Spacer used in the conjugate | Geometric mean anti-MCPS antibody level, units/mL (CI)* | Fold increase over control group |
|---|---|---|---|
| Native Mn C PS (control) | — | 16 (8, 34) | — |
| Conjugate MC6xTTH | Hydrazine | 2141 (1096, 4285) | 134 |
| Conjugate Mix TTHb | Hydrazine | 4228 (2189, 8167) | 264 |
| Conjugate MC6xTTADH | ADH | 1092 (655, 1820) | 68 |
| Conjugate Mix bTTADH | ADH | 3977 (2423, 6526) | 248 | a. The geometric mean anti-Mn C PS antibody levels (compared to a reference serum with anti-MN C PS antibody level of 3200 units/mL) with 1 SD confidence interval of mouse groups (10 mice per group) two weeks post $2^{nd}$ immunization with 1 μg/dose native Mn C PS or each of the four Mn C PS-TT conjugates.

Method A—Meningococcus Group A Conjugate

Activation of TT to Contain Hydrazide Groups

Tetanus toxoid (4.2 mg/mL) is activated with 0.42 M hydrazine in the presence of 20 mM EDC, 0.1 M MES, pH 6.5 at 20-24° C. After reaction for 4 hours, the pH of the reaction mixture was raised to 7.5-10 with 1 N NaOH to stop the reaction. The reaction mixture is buffer-exchanged with 30 mM NaCl, 3 mM Na2CO3, pH about 10.5 at 4° C. using a 12-14 KDa dialysis membrane. The protein concentration of the resulting TT-hydrazide sample was determined by Lowry assay (see Pierce Catalog 2003-2004, page 306) using bovine serum albumin as a standard. The hydrazide content was determined by TNBS assay using adipic acid dihydrazide as a standard, as described in Vidal, J. Immunol. Methods 1986; 86:155-156. The degree of activation of TT so prepared was approximately 50 hydrazide groups perTT molecule.

Activation of Mn A PS to Contain Aldehyde Groups

Mn A PS (10 mg/mL in 25 mM HEPES, pH 7.4) was reacted with 6 mM $NaIO_4$ at 20-24° C. for 4 hours. The sample was dialyzed against 10 mM HEPES, pH 7.4 at 4° C. using a 12-14 KDa dialysis membrane. The concentration of the resulting activated PS was determined by phosphorus assay, as described in Keleti et al, Handbook of micromethods for the biological sciences. 70. Phosphorus (Total). Page 84. Van Nostrand Reinhold Co., New York, 1974. The aldehyde content of the activated PS was determined by BCA assay (Pierce Catalog 2003-2004, pages 241 and 305) using glucose as a standard. The degree of activation of the activated Mn A PS prepared by this protocol was approximately one aldehyde group per 80 to 110 monomelic repeating units.

Conjugation of Activated Mn A PS to Activated TT

An aliquot of hydrazide-containing TT was adjusted to 10 mg/mL by lyophilization and dissolution in water. An aliquot of aldehyde-containing Mn CPS was adjusted to 10 mg/mL by lyophilization and dissolution in 0.2 M HEPES, pH 7.5, 30 mM EDTA. Activated TT solution was added to equal volume of the activated Mn A PS and vortexed. The reaction mixture was incubated at 20-24° C. for 18 hours. The reaction mixture was treated with $NaBH_4$. (10-fold molar equivalent to initial aldehyde concentration in the activated PS) for 6 hours. The solution was buffer-exchanged with saline, 10 mM HEPES, pH 7.5, 1 mM EDTA using a 12-14 KDa molecular weight cut-off membrane. Total protein was determined by Lowry assay (see Pierce Catalog 2003-2004, page 306) using bovine serum albumin as a standard. The total Mn A PS content was determined by phosphorus assay, as described in Keleti et al., Handbook of micromethods for the biological sciences. 70. Phosphorus (Total). Page 84. Van Nostrand Reinhold Co., New York, 1974. Several preparations of Mn A PS-TT conjugates were made. The HPSEC profile of one of these conjugates and the activated TT are shown in FIG. 6.

Immunogenicity of Mn A PS-TT Conjugates

These Mn A PS-TT conjugate preparations and native Mn A PS (control) were separately used to immunize groups of 10 mice at 1 μg polysaccharide/dose on days 0 and 14. The geometric means of the induced antibody levels (units/mL) two weeks post $2^{nd}$ injection are 79 units/mL for native PS control group and 11,000-47,000 units/mL for the conjugate groups, assuming 3200 units/mL for the reference serum (Table 5). The conjugates induced 169-595 fold more anti-Mn A PS specific antibody in mice as compared to the native Mn A PS control.

TABLE 5

| Mouse groups of different conjugate and polysaccharide immunogens | Geometric mean anti-MAPS antibody level in units/mL (CI)* | Fold increase over control group |
|---|---|---|
| Native Mn A PS (control) | 79 (21, 290) | — |
| MA031209R | 14,861 (6542, 33757) | 188 |
| MA031209B | 13,375 (7677, 23303) | 169 |
| MA031212B | 14,777 (5433, 40191) | 187 |
| MA031212J | 13,385 (5150, 34789) | 169 |
| MA031216B | 15,052 (4910, 46149) | 191 |
| MA031216J | 11,074 (4605, 26628) | 140 |
| MA031219R | 20,410 (9282, 44884) | 258 |
| MA031219B | 13,813 (4645, 41071) | 175 |
| MA031219J | 26,826 (9172, 78463) | 340 |
| MA031221R | 18,994 (8012, 45030) | 240 |
| MA031221B | 42,041 (25208, 73147) | 532 |
| MA031221J | 46,981 (20238, 109062) | 595 | a. The geometric mean anti-Mn A PS antibody levels (compared to a reference serum with anti-Mn A PS antibody level of 3200 units/mL) with 1 SD confidence interval of mouse groups (10 mice per group) two weeks post $2^{nd}$ immunization with 1 μg/dose native Mn A PS or each of the four Mn A PS-TT conjugates.

Method B—Pneumococcal Type 6B Conjugate

Activation of TT to Contain Hydrazide Groups

Tetanus toxoid (4.2 mg/mL) was activated with 0.42 M hydrazine in the presence of 20 mM EDC, 0.1 M MES, pH 6.5 at 20-24° C. After reaction for 4 hours, the pH of the reaction mixture was raised to 7.5-10 with 1 N NaOH to stop the reaction. The reaction mixture was buffer-exchanged with 30 mM NaCl, 3 mM $Na_2CO_3$, pH about 10.5 at 4° C. using a 12-14 KDa dialysis membrane. The protein concentration of the resulting TT-hydrazide sample was determined by Lowry assay (Pierce Catalog 20032004, page 306) using bovine serum albumin as a standard. The hydrazide content was determined by TNBS assay using adipic acid dihydrazide as a standard, as described in Vidal, J. Immunol. Methods 1986; 86:155-156. The degree of activation of TT so prepared is approximately 50 hydrazide groups per TT molecule.

Activation of Pn 6B PS to Contain Cyanate Groups

Pn 6B polysaccharide (0.4 mL, 10 mg/mL) was activated with 38 μL CDAP (100 mg/mL in acetonitrile) for 2-2.5 minutes at 20-24° C. in the presence of 38 μL 0.2 M triethylamine. The activated polysaccharide was mixed with 5 mL ice-cold 0.2 M HEPES, pH 7.5, 30 mM EDTA, and immediately used for conjugation.

Conjugation of Activated Pn 6B PS to Activated TT

The activated polysaccharide was added to 2 mg activated TT (ice-cold, 0.5 mL, 4 mg/mL); vortex. After incubating at 4° C. with gentle shaking for 36 hours, the reaction mixture was incubated at 20-24° C. for another 18 hours. The prolonged incubation ensured decomposition of any residual unreacted cyanate groups. The solution was buffer-exchanged with saline, 10 mM HEPES, pH 7.5, 1 mM EDTA using a 12-14 KDa molecular weight cut-off membrane. The total protein content is determined by Lowry assay (Pierce Catalog 2003-2004, page 306), and the total polysaccharide content was determined by anthrone assay, as described by Keleti et al., Handbook of micromethods for the biological sciences. 61. Hexoses (Anthrone). Page 73. Van Nostrand Reinhold Co., New York, 1974. The HPSEC profiles of Pn 6B PS-TT and the activated TT are shown in FIG. 7.

Immunogenicity of Pn 6B PS-TT Conjugate

The Pn 6B PS-TT conjugate as prepared above and native Pn 6B PS (control) were separately used to immunize groups of 10 mice at 1 μg polysaccharide/dose on days 0, 14 and 28. The geometric means of the induced antibody levels (units/mL) two weeks post $3^{rd}$ injection were 13 units/mL for native Pn 6B PS control group and 3,700 units/mL for the Pn 6B PS-TT conjugate group, assuming 3200 units/mL for the reference serum (Table 6). The conjugate induced 285 fold anti-Pn 6B PS specific antibody in mice as compared to the native Pn 6B PS control.

TABLE 6

| Mouse groups of different conjugate and polysaccharide immunogens | Geometric mean anti-MAPS antibody level in units/mL (CI*) | Fold increase over control group |
|---|---|---|
| Native Pn 6B PS (control) | 13 (10, 17) | — |
| Pn 6B PS-TT | 3,700 (240, 5,705) | 258 | a. The geometric mean anti-Pn 6B PS antibody levels (compared to a reference serum with anti-Pn 6B PS antibody level of 3200 unites/mL) with 1 SD confidence interval of mouse groups (10 mice per group) two weeks post third immunization with 1 µg/dose native Pn 6B PS or the Pn 6B PS-TT conjugate.

Method B—Pneumococcal Type 7F Conjugate

Activation of TT to Contain Hydrazide Groups

Tetanus toxoid (4.2 mg/mL) was activated with 0.42 M hydrazine in the presence of 20 mM EDC, 0.1 M MES, pH 6.5 at 20-24° C. After reaction for 4 hours, the pH of the reaction mixture was raised to 7.5-10 with 1 N NaOH to stop the reaction. The reaction mixture was buffer-exchanged with 30 mM NaCl, 3 mM $Na_2CO_3$, pH about 10.5 at 4° C. using a 12-14 KDa dialysis membrane. The protein concentration of the resulting TT-hydrazide sample was determined by Lowry assay (Pierce Catalog 2003-2004, page 306) using bovine serum albumin as a standard. The hydrazide content was determined by TNBS assay using adipic acid dihydrazide as a standard, as described in Vidal, J. Immunol. Methods 1986; 86:155-156. The degree of activation of TT so prepared was approximately 50 hydrazide groups per TT molecule.

Activation of Pn 7F PS to Contain Cyanate Groups

Pn 7F polysaccharide (0.4 mL, 10 mg/mL) was activated with 38 µL CDAP (100 mg/mL in acetonitrile) for 2-2.5 minutes at 20-24° C. in the presence of 38 µL 0.2 M triethylamine. The activated polysaccharide was mixed with 5 mL ice-cold 0.2 M HEPES, pH 7.5, 30 mM EDTA, and immediately used for conjugation.

Conjugation of Activated Pn 7F PS to Activated TT

The activated polysaccharide was added to 2 mg activated TT (ice-cold, 0.5 mL, 4 mg/mL) and vortexed. After incubating at 4° C. with gentle shaking for 36 hours, the reaction mixture was incubated at 20-24° C. for another 18 hours. The prolonged incubation ensured decomposition of any residual unreacted cyanate groups. The solution was buffer-exchanged with saline, 10 mM HEPES, pH 7.5, 1 mM EDTA using a 12-14 KDa molecular weight cut-off membrane. Total protein content was determined by Lowry assay (Pierce Catalog 2003-2004, page 306). Total polysaccharide content was determined by anthrone assay, as described by Keleti et al., Handbook of micromethods for the biological sciences. 61. Hexoses (Anthrone), Page 73, Van Nostrand Reinhold Co., New York, 1974. The HPSEC profiles of Pn 7F PS-TT and the activated TT are shown in FIG. 8.

Immunogenicity of Pn 7F PS-TT Conjugate

The Pn 7F PS-TT conjugate prepared as described above and native Pn 7F PS (control) were separately used to immunize groups of 10 mice at 1 µg polysaccharide/dose on days 0, 14 and 28. The geometric means of the induced antibody levels (units/mL) two weeks post $3^{rd}$ injection are 17 units/mL for native Pn 7F PS control group and 17,077 units/mL for the Pn 7F PS-TT conjugate group, assuming 3200 units/mL for the reference serum (Table 7). The conjugate induced 1,005 fold anti-Pn 7F PS specific antibody in mice as compared to the native Pn 7F PS control.

TABLE 7

| Mouse groups of different conjugate and polysaccharide immunogens | Geometric mean anti-MAPS antibody level in units/mL (CI)* | Fold increase over control group |
|---|---|---|
| Native Pn 7F PS (control) | 17 (14, 20) | — |
| Pn 7F PS-TT | 17,077 (8,034, 36,299) | 1,005 | a. The geometric mean anti-Pn 7F PS antibody levels (compared to a reference serum with anti-Pn 7F PS antibody level of 3200 units/mL) with 1 SD confidence interval of mouse groups (10 mice per group) two weeks post third immunization with 1 µg/dose native Pn 7F PS or the Pn 7F PS-TT conjugate.

Method C—Pneumococcal Serotype 9V Conjugate

Activation of TT to Contain Aldehyde Groups

Tetanus toxoid (4.2 mg/mL) was activated with 0.42 M 1-amino-2,3-propanediol (APDO) in the presence of 20 mM EDC, 0.1 M MES, pH 6.5 at 20-24° C. After reacting for 4 hours, the pH of the reaction mixture was raised to 7.5-10 with 1 N NaOH to stop the reaction. The reaction mixture was buffer-exchanged with 30 mM NaCl, 3 mM $Na_2CO_3$, pH about 10.5 at 4° C. using a 12-14 KDa dialysis membrane. The degree of TT modification with APDO is determined by purpald assay (as described in Lee et al., Anal. Biochem. 2001; 296:73-82) and Lowry assay (Pierce Catalog 2003-2004, page 306). An aliquot of TT-APDO was reacted with 6 mM $NaIO_4$ for 1 hour and then buffer exchanged with 30 mM NaCl, 3 mM $Na_2CO_3$, pH about 10.5. The degree of activation of TT prepared was approximately 26 APDO or aldehyde groups per TT molecule.

Activation of Pn 9V PS to Contain Hydrazide Groups

Pn 9V PS (0.4 mL, 10 mg/mL) was activated with 364 CDAP (100 mg/mL in acetonitrile) for 2-2.5 minutes at 20-24° C. in the presence of 36 µL 0.2 M triethylamine. At the end of activation, 0.4 mL 0.5 M ADH was added and mixed. The reaction mixture was incubated 18 hours at 20-24° C. The sample was dialyzed against 10 mM HEPES, pH 7.5 at 4° C. using a 12-14 KDa dialysis membrane. The PS concentration is determined by anthrone assay, as described in Keleti et al., Handbook of micromethods for the biological sciences. 61. Hexoses (Anthrone), Page 73. Van Nostrand Reinhold Co., New York, 1974. The hydrazide content was determined by TNBS assay using adipic acid dihydrazide as a standard, as described in Vidal, J. Immunol. Methods 1986; 86:155-156. The degree of activation of the activated Pn 9V PS prepared by this protocol was approximately one hydrazide group per saccharide repeating unit.

Conjugation of Activated Pn 9V PS to Activated TT

An aliquot of hydrazide-containing Pn 9V PS (1 mg; 0.236 mL 4.233 mg/mL) was mixed with 0.067 mL 1 M HEPES, pH 7.5 and 0.068 mL $H_2O$. An aliquot of aldehyde-containing TT (1 mg; 0.296 mL 3.38 mg/mL) was added to the activated Pn 9V PS (Total volume, 0.67 mL; initial concentration for both reactants, 1.5 mg/mL). The reaction mixture was incubated at 20-24° C. for 18 hours. The reaction mixture was treated with $NaBH_4$ (10-fold molar equivalent to initial aldehyde concentration in the activated PS) for 6 hours. The solution was buffer-exchanged with saline, 10 mM HEPES, pH 7.5, 1 mM EDTA using a 12-14 KDa molecular weight cut-off membrane. Total protein was determined by Lowry assay (Pierce Catalog 2003-2004, page 306) using bovine serum albumin as a standard. Total Pn 9V PS content was determined by anthrone assay, as described by Keleti et al., Handbook of micromethods for the biological sciences. 61. Hexoses (Anthrone), Page 73, Van Nostrand Reinhold Co., New York, 1974. The HPSEC profiles of Pn 9V PS-TT and the activated TT are shown in FIG. 9.

Immunogenicity of Pn 9V PS-TT Conjugate

These Pn 9V PS-TT conjugate and native Pn 9V PS (control) were separately used to immunize groups of 10 mice at 1 µg polysaccharide/dose on days 0, 14 and 28. The geometric means of the induced antibody levels (units/mL) two weeks post $3^{rd}$ injection are 15 units/mL for native Pn 9V PS control group and 13,291 units/mL for the Pn 9V PS-TT conjugate group, assuming 3200 units/mL for the reference serum (Table 8). The conjugate induced 886 fold anti-Pn 9V PS specific antibody in mice as compared to the native Pn 9V PS control.

TABLE 8

| Mouse groups of different conjugate and polysaccharide immunogens | Geometric mean anti-MAPS antibody level in units/mL (CI)* | Fold increase over control group |
|---|---|---|
| Native Pn 9V PS (control) | 15 (14, 16) | — |
| Pn 9V PS-TT | 13,291 (6,339, 27,869) | 886 | a. The geometric mean anti-Pn 9V PS antibody levels (compared to a reference serum with anti-Pn 9V PS antibody level of 3200 units/mL) with 1 SD confidence interval of mouse groups (10 mice per group) two weeks post third immunization with 1 µg/dose native Pn 9V PS or the Pn 9V PS-TT conjugate.

All references cited herein are incorporated herein by reference in their entirety. To the extent publications and patents or patent applications incorporated by reference contradict the disclosure contained in the specification, the specification is intended to supersede and/or take precedence over any such contradictory material.

The term "comprising" as used herein is synonymous with "including," "containing," or "characterized by," and is inclusive or open-ended and does not exclude additional, unrecited elements or method steps.

All numbers expressing quantities of ingredients, reaction conditions, and so forth used in the specification and claims are to be understood as being modified in all instances by the term "about." Accordingly, unless indicated to the contrary, the numerical parameters set forth in the specification and attached claims are approximations that can vary depending upon the desired properties sought to be obtained by the present invention. At the very least, and not as an attempt to limit the application of the doctrine of equivalents to the scope of the claims, each numerical parameter should be construed in light of the number of significant digits and ordinary rounding approaches.

The above description discloses several methods and materials of the present invention. This invention is susceptible to modifications in the methods and materials, as well as alterations in the fabrication methods and equipment. Such modifications will become apparent to those skilled in the art from a consideration of this disclosure or practice of the invention disclosed herein. Consequently, it is not intended that this invention be limited to the specific embodiments disclosed herein, but that it cover all modifications and alternatives coming within the true scope and spirit of the invention as embodied in the attached claims.

What is claimed is:

1. A method for preparing a conjugate vaccine, the method comprising:
    reacting a protein with 1-amino-2,3-propanediol (APDO) in the presence of 1-(3-(dimethylamino)propyl]-3-ethyl carbodiimide hydrochloride at a pH of from about 6 to about 7, whereby a solution of a APDO-modified protein is obtained;
    buffer exchanging the solution of the APDO-modified protein to a pH of from about 10.0 to about 11.0;
    reacting the APDO-modified protein with an oxidizing agent, whereby a solution of an aldehyde-activated protein is obtained;
    buffer exchanging the solution of the aldehyde-activated protein to a pH of from about 10.0 to about 11.0;
    reacting a hydrazide-activated polysaccharide with the aldehyde-activated protein at a pH of from about 6 to about 8, whereby a conjugate comprising one or more C═N double bonds is obtained; and
    reducing the C═N double bonds of the conjugate to C—N single bonds, whereby a conjugate vaccine capable of stimulating an immune response is obtained.

2. The method according to claim 1, wherein the polysaccharide is selected from the group consisting of Meningococcal polysaccharides, Pneumococcus polysaccharides, *Hemophilus influenzae* type b polysaccharide, Vi polysaccharide of *Salmonnella typhi*, and group B *Streptococcus* polysaccharides.

3. The method according to claim 1, wherein the protein is selected from the group consisting of tetanus toxoid, diptheria toxoid, $CRM_{197}$, and meningococcal protein.

4. The method according to claim 1, wherein the hydrazide-activated polysaccharide is prepared by:
    reacting a polysaccharide with an oxidizing agent in a solution, whereby an aldehyde-activated polysaccharide is obtained;
    reacting the aldehyde-activated polysaccharide with adipic acid dihydrazide to yield an intermediate comprising one or more C═N double bonds; and
    reducing the C═N double bonds of the intermediate to C—N single bonds, whereby a hydrazide-activated polysaccharide is obtained.

5. The method according to claim 1, wherein the hydrazide-activated polysaccharide is prepared by:
    reacting a polysaccharide with 1-cyano-4-dimethylammoniumpyridinium tetrafluoroborate, whereby a cyanate-functionalized polysaccharide is obtained;
    reacting the cyanate-functionalized polysaccharide with adipic acid dihydrazide, whereby a hydrazide-activated polysaccharide is obtained.

6. The method according to claim 1, wherein the hydrazide-activated polysaccharide is prepared by:
    reacting a polysaccharide with adipic acid dihydrazide in the presence of 1-[3-(dimethylamino)propyl]-3-ethyl carbodiimide hydrochloride, whereby a hydrazide-activated polysaccharide is obtained.

7. A conjugate vaccine, the conjugate vaccine comprising at least one polysaccharide moiety and at least one protein moiety, wherein the polysaccharide moiety is linked to the protein moiety through at least one linking group of the formula —C(═O)—NH—CH₂—CH₂—NH—NH—.

8. The conjugate vaccine of claim 7, wherein the conjugate vaccine comprises a plurality of polysaccharide moieties and a plurality of protein moieties crosslinked to form a lattice structure by a plurality of linking groups.

9. The conjugate vaccine of claim 7, wherein the polysaccharide is selected from the group consisting of Meningococcal polysaccharides, Pneumococcus polysaccharides, *Hemophilus influenzae* type b polysaccharide, Vi polysaccharide of *Salmonnella typhi*, and group B *Streptococcus* polysaccharides.

10. The conjugate vaccine of claim 7, wherein the protein is selected from the group consisting of tetanus toxoid, diptheria toxoid, $CRM_{197}$, and meningococcal protein.

* * * * *